(12) United States Patent
Kelley et al.

(10) Patent No.: US 11,160,770 B2
(45) Date of Patent: Nov. 2, 2021

(54) COMPOUNDS, COMPOSITIONS AND METHODS FOR TREATING OXIDATIVE DNA DAMAGE DISORDERS

(71) Applicant: Indiana University Research and Technology Corporation, Indianapolis, IN (US)

(72) Inventors: Mark R. Kelley, Zionsville, IN (US); Michael R. Vasko, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/822,466

(22) Filed: Mar. 18, 2020

(65) Prior Publication Data

US 2020/0215001 A1    Jul. 9, 2020

Related U.S. Application Data

(60) Continuation of application No. 16/416,518, filed on May 20, 2019, now abandoned, which is a division of application No. 15/411,450, filed on Jan. 20, 2017, now abandoned, which is a continuation of application No. 15/011,016, filed on Jan. 29, 2016, now abandoned, which is a continuation of application No. 14/122,313, filed as application No. PCT/US2012/040515 on Jun. 1, 2012, now abandoned.

(60) Provisional application No. 61/493,169, filed on Jun. 3, 2011.

(51) Int. Cl.
| | |
|---|---|
| *A61K 31/122* | (2006.01) |
| *A61K 31/12* | (2006.01) |
| *C07C 66/00* | (2006.01) |
| *C07C 235/78* | (2006.01) |
| *C07D 295/185* | (2006.01) |
| *A61K 31/16* | (2006.01) |
| *A61K 31/165* | (2006.01) |
| *A61K 31/19* | (2006.01) |
| *A61K 31/192* | (2006.01) |
| *A61K 31/20* | (2006.01) |
| *A61K 31/21* | (2006.01) |
| *A61K 31/495* | (2006.01) |
| *A61K 31/5375* | (2006.01) |

(52) U.S. Cl.
CPC ............ *A61K 31/122* (2013.01); *A61K 31/12* (2013.01); *A61K 31/16* (2013.01); *A61K 31/165* (2013.01); *A61K 31/19* (2013.01); *A61K 31/192* (2013.01); *A61K 31/20* (2013.01); *A61K 31/21* (2013.01); *A61K 31/495* (2013.01); *A61K 31/5375* (2013.01); *C07C 66/00* (2013.01); *C07C 235/78* (2013.01); *C07D 295/185* (2013.01)

(58) Field of Classification Search
CPC ............................. A61K 31/122; A61K 31/12
See application file for complete search history.

(56) References Cited

U.S. PATENT DOCUMENTS

| | | | |
|---|---|---|---|
| 4,388,312 A | 6/1983 | Terao et al. | |
| 4,533,554 A | 8/1985 | Terao et al. | |
| 5,210,239 A | 5/1993 | Abe et al. | |
| 5,385,942 A | 1/1995 | Abe et al. | |
| 5,627,165 A | 5/1997 | Glazier | |
| 5,849,793 A | 12/1998 | Pan et al. | |
| 5,919,643 A | 7/1999 | Kelley et al. | |
| 6,190,661 B1 | 2/2001 | Kelley et al. | |
| 6,406,917 B1 | 6/2002 | Kelley et al. | |
| 6,433,199 B1 | 8/2002 | Ono et al. | |
| 9,040,505 B2 | 5/2015 | Kelley et al. | |
| 9,089,605 B2 | 6/2015 | Kelley et al. | |
| 9,193,700 B2 | 6/2015 | Kelley et al. | |
| 2003/0091574 A1 | 5/2003 | Gevas et al. | |
| 2003/0229004 A1 | 12/2003 | Zarling et al. | |
| 2004/0002499 A1 | 1/2004 | Aggarwal | |
| 2005/0186208 A1 | 8/2005 | Fyfe et al. | |
| 2010/0297113 A1 | 11/2010 | Kelley et al. | |

FOREIGN PATENT DOCUMENTS

| | | | |
|---|---|---|---|
| EP | 0025692 A1 | | 3/1981 |
| EP | 0301861 A1 | | 2/1989 |
| EP | 0737671 A2 | | 10/1996 |
| JP | 2011028156 A | * | 4/2009 |
| WO | 1999048860 A1 | | 9/1999 |
| WO | 2001000229 A1 | | 1/2001 |
| WO | 2009042542 A1 | | 4/2009 |
| WO | 2009042544 A1 | | 4/2009 |
| WO | WO 2009042544 A1 | * | 7/2009 |
| WO | 2012022467 A1 | | 2/2012 |

OTHER PUBLICATIONS

Song et al., A new synthetic route to 2H-benzo[g]chromene-5,10-diones involving ring closing metathesis, Journal of Heterocyclic Chemistry (2009), 46(2), 207-212.*

STN document No. 154:247336, status date Nov. 20, 2020.*

Nyland et al., Design and Synthesis of Novel Quinone Inhibitors Targeted to the Redox Function of Apurinic/Apyrimidinic Endonuclease 1/Redox Enhancing Factor-1 (Ape1/Ref-1), J. Med. Chem. 2010, 53, 3, 1200-1210.*

STN document No. 126:211950 for Anufriev et al., Synthetic Communications (1997), 27(1), 119-126.*

STN document No. 111:112073 for Lessmann et al., New juglomycins, Zeitschrift fuer Naturforschung, B: Chemical Sciences, (1989), 44(3), 353-63.*

(Continued)

*Primary Examiner* — Svetlana M Ivanova
(74) *Attorney, Agent, or Firm* — Stinson LLP

(57) ABSTRACT

Compounds, compositions, and formulations, and accompanying methods useful for treating disorders arising from oxidative DNA damage, including oxidative DNA damage resulting from ionizing radiation or other therapy are described herein.

19 Claims, 4 Drawing Sheets

(56) References Cited

OTHER PUBLICATIONS

STN document No. 109:110085 for Reed et al., Efficient synthesis of furochromone and furocoumarin natural products (khellin, pimpinellin, isophellopterin) by thermal rearrangement of 4-furyl-4-hydroxycyclobutenones, Journal of Organic Chemistry (1988), 53(18), 4166-71.*
STN document No. 69:35797 for Heinz et al., Journal of Pharmaceutical Sciences (1968), 57(3), 520-3.*
STN document No. 64:19019 for Russell et al., Chemical Communications (London) (1965), (21), 529-30.*
STN document No. 53:77719 for Kuroda et al., Proceedings of the Japan Academy (1958), 34, 616-18.*
STN document No. 53:77718 for Pitombo, Chemische Berichte (1959), 92, 745-9.*
STN document No. 18:12193 for Berichte der Deutschen Chemischen Gesellschaft [Abteilung] B: Abhandlungen (1923), 56B, 2548-55.*
Alka et al., Synthesis of novel 2-substituted 1,4-napthoquinones using Heck reaction in green reaction media; Arkivoc Journal, vol. 11, 2006, pp. 99-106.
Bapat et al., Novel small molecule inhibitor of ApeI endonuclease blocks proliferation and reduces viability of glioblastoma cells, J Pharmacol Exp Tuer., vol. 334 (2010) pp. 988-998.
Barbosa et al., New 1,2,3,4-tetrahydro-1-aza-anthraquinones and 2-aminoalkyl compounds from norlapachol with molluscidal activity, Bioorganic & Medicinal Chemistry, vol. 13, 2005, pp. 6464-6469.
Belzile et al., Targeting DNA Repair Proteins: A Promising Avenue for Cancer Gene Therapy, Current Gene Therapy, vol. 6 (2006) pp. 111-123.
Bobola et al., Apurinic/apyrimidinic endonuclease activity is elevated in human adult gliomas. Clinical Cancer research, vol., No. 11, (2001) pp. 3510-3518.
Bondeinell et al., Synthesis of 2-methyl-3-vinyl-1,4-naphtoquinones; The Journal of Organic Chemistry, vol. 33, No. 12, 1998, pp. 4351-4362.
Boudalis et al., Synthesis, Spectroscopic, structural and electrochemical studies of carboxyl substituted 1,4-hapthoquinones, Inorganic Chimica Acta, 2008, vol. 361, pp. 1681-1688.
Brain S.D., Sensory neuropeptides: their role in inflammation and would healing; Immunopharmacology; 1997, vol. 37, pp. 133-152.
Brewer et al., Optimized survival of hippocampal neurons in B27-supplemented Neurobasal, a new serum-free medium combination, J Neurosci Res, vol. 35 (1993) pp. 567-576.
Chen et al., Peptidase inhibitors improve recovery of substance P and calcitonin gene-related peptide release from rat spinal cord slices, Peptides, vol. 17 (1996) pp. 31-37.
Commandeur et al., Study of radical decarboxylation toward functionalization of naphthoquinones; Eur. J. Org. Chem., 2007, pp. 3045-3052.
Crowe et al., Radiation-induced changes in neuropeptides in the rat urinary bladder, J Urol, vol. 156 (1996) pp. 2062-2066.
Cunha et al., Synthesis of novel napthoquinone-spermidine conjugates and their effects on DNA-topoisomerase II and I-alpha, J Braz. Chem. Soc. vol. 17, No. 3, pp. 439-442, 2006.
Database WPI Section Ch, Week 1995 1996, Thomson Scientific, London, GB; AN 1996-017132 Goto Masaki et al.: NfkB transcription factor inhibitor & JP 07 291859 A (Eisai Co Ltd) Nov. 7, 1995 Nov. 7, 1995).
Dietrich et al., Clinical Patterns and Biological Correlates of Cognitive Dysfunction Associated with Cancer Therapy, Oncologist, vol. 13 (2008) pp. 1285-1295.
Evans et al., Going APE over ref-1, Mutation research, vol. 461 (2000) pp. 83-108.
Fayette et al., Use of angiogenesis inhibitors in tumour treatment European Journal of Cancer, 40 Pergamon Press, Oxford, GB, vol. 41, No. 8, 2005, pp. 1109-1116.
Fishel et al., DNA repair in neurons: so if they don't divide what's to repair?, Mutation research, vol. 614 (2007) pp. 24-36.
Fishel et al., Impact of APE1/Ref-1 redox inhibition on pancreatic tumor growth. Molecular cancer herapeutics, vol. 10, No. 9 (2011) pp. 1698-1708.
Fishel et al., The DNA base excision repair protein Apel/Ref-1 as a therapeutic and chemopreventive target. Molecular Aspects of Medicine Jun.-Aug. 2007, vol. 28, No. 3-4, pp. 375,395.
Florea et al., Cisplatin as an Anti-Tumor Drug: Cellular Mechanisma of Activity, Drug Resistance and Induced Side Effects; Cancers; 2011, vol. 3, pp. 1351-1371.
Georgiadis et al., Evolution of the redox function in mammalian Apurinic/apyrimidinic Mutation research, vol. 643 (2008) pp. 54-63.
Gilmore et al., Glial-glial and glial-neuronal interfaces in radiation-induced, glia-depleted spinal cord, J Anat, 190 ( Pt 1) (1997) pp. 5-21.
Gobbel et al., Neuronal death is an active, caspase-dependent process after moderate but not severe DNA damage, J Neurochem, vol. 76 (2001) pp. 520-531.
Goldstein et al., NF-L and peripherin immunoreactivities define distinct classes oral sensory ganglion cells, J Neurosci Res, vol. 30 (1991) pp. 92-104.
Golo et al., Inhibitory Effect of E3330, a Novel quinine Derivative Able to Suppress Tumor Necrosis Factor-a Generation, on Activation of Nuclear Factor-KB, Molecular Pharmacology, vol. 49; pp. 860-873 (1996).
Hiramoto et al., Nuclear targeted suppression of NF-kappa B activity by the novel quinone derivative E3330, J Immunol, vol. 160 (1998) pp. 810-819.
Hockerfelt et al., Parallel increase in substance P and VIP in rat duodenum in response to irradiation, Peptides, vol. 21 (2000) pp. 271-281.
Hochberg et al., Neuropsychologic impairment in astrocytoma survivors, Neurology, vol. 30, (1980) pp. 172-177.
Holzer et al., Local effector functions of capsaicin-sensitive sensory nerve endings: involvement of tachykinins, calcitonin gene-related peptide and other neuropeptides, Neuroscience, vol. 24 (1988) pp. 739-768.
Hsieh et al., Activation of APE/Ref-1 redox activity is mediated by reactive oxygen species and PKC phosphorylation, Nucleic Acids Res, vol. 29 (2001) pp. 3116-3122.
Jiang et al., Small Molecule Targeting the Hec1/Nek2 Mitotic Pathway Suppresses Tumor Cell Growth in Culture and in Animal; Cancer Res, 2008, vol. 68, No. 15.
Jiang et al. "Role of APE1 in Differentiated Neuroblastoma SH-SY5Y Cells in Response to Oxidative Stress: Use of APE1 Small Molecule Inhibitors to Delineate APE1 Functions" DNA Repair. 2009. vol. 8, pp. 1273-1282.
Jiang et al., Inhibition of APEI/Ref-1 Redox Activity with APX3330 Blocks Retinal Angiogenesis in vitro and in vivo, Vision Res, vol. 51 (2011).
Jiang et al., Implications of Apurinic/Apyrimidinic Endonuclease in Reactive Oxygen Signaling Response after Cisplatin Treatment of Dorsal Root Ganglion Neurons, Cancer Res, vol. 68 (2008) pp. 6425-6434.
Kaiser et al., First Pass at Cancer Genome Reveals Complex Landscape, Science, vol. 313, Sep. 8, 2006, p. 1370.
Kakolyris et al., Human AP endonuclease 1 (HAP1) protein expression in breast cancer correlates with lymph node status and angiogenesis. British journal of cancer, vol. 77, No. 7 (1998) pp. 1169.
Kelly et al., Abstracts, 36th Central Regional Meeting of the Amer. Chem. Soc. Jun. 2-4, 2004.
Kelley et al, DNA repair proteins as molecular targets for cancer therapeutics, Anticancer Agents Med Chem, vol. 8 (2008) pp. 417-425.
Kelley et al., Functional analysis of new and novel analogs of E3330 that block the redox signaling activity of the multifunctional AP endonuclease/redox signaling enzyme APEI/Ref-1, Antioxid Redox Signal (2011).
Koukouakis et al., Nuclear expression of human apurinic/apyrimidinic endonuclease (HAP1/Ref-1) in head and neck cancer is associated with resistance to chemo-radiolherapy and poor Julcome. Int J Radial Oncol Biol Phys. 2001; vol. 50, pp. 27-36.

(56) References Cited

OTHER PUBLICATIONS

Luo et al., Redox Regulation of DNA Repair: Implications for Human Health and Cancer Therapeutic Development, Antioxid Redox Signal, vol. 12 (2010) pp. 1247-1269.

Luo et al., Role of the multifunctional DNA repair and redox signaling protein Ape1/Ref-1 in cancer and endolhelial cells: small-molecule inhibition of the redox function of Ape1 . Antioxidants & redox signaling, vol. 10, No. 11 (2008), pp. 1853-1867.

Luo et al., Inhibition of the human apurinic/apyrimidinic endonuclease DNA base excision repair enzyme/edox factor (APE1/Ref-1) using small molecule redox and repair inhibitors: Therapeutic implications Proceedings of the Annual Meeting of the American Association for Cancer Research, New York, NY, vol. 15, pp. 703-704.

Madsen et al., Arrested neuronal proliferation and impaired hippocampal function following fractionated brain irradiation in the adult rat, Neuroscience, 119 (2003) 635-642.

Mattson et al., Cellular and Molecular Mechanisms Underlying Perturbed Energy Metabolism and Neuronal Degeneration in Alzheime?s and Parkinson's Diseases, Annals of the New York Academy of Sciences, Nov. 1999, pp. 154-175.

McNeill et al., A Dominant-Negative Form of the Major Human Abasic Endonuclease Enhances Cellular Sensitivity to Laboratory and Clinical DNA-Damaging Agents, Mol Cancer Res, vol. 5 (2007) pp. 61-70.

Mima et al., Characterization of 5' flanking region of alpha isoform of rat Ca2+/calmodulin-dependent protein kinase II gene and neuronal cell type specific promoter activity, Neurosci Lett, vol. 307 (2001) pp. 117-121.

Mital et al., Synthesis and biological evaluation of substituted naphthoquinone derivatives as potent antimyobacterial agents, Arkivoc, 2008, vol. 16, pp. 176-192.

Mozes A., Cancer Survivors May Be at Risk for Memory Problems, in: Health Day News, 2010.

Nyland et al., Design and Synthesis of Novel Quinone Inhibitors Targeted to the Redox Function of Apurinic/Apyrimidinic Endonuclease 1/Redox Enhancing Factor-1 (Ape1/Ref-1), Journal of medicinal chemistry, vol. 53 (2010) pp. 1200-1210.

Paap et al., Human abasic endonuclease action on multilesion abasic clusters: implications for radiation-induced biological damage, Nucl. Acids Res., (2008) gknl 18.

Puglisi et al., Prognostic role of Ape/Ref-1 subcellular expression in stage 1-111 breast carcinomas. Oncology eports vol. 9, No. 1 (2002) pp. 11-17.

Puglisi et al., Prognostic significance of Ape1/ref-1 subcellular localization in non-small cell lung carcinomas. Anticancer research, vol. 21, No. 6A (2000) pp. 4041-4049.

Raber et al., Radiation-induced cognitive impairments are associated with changes in indicators of hippocampal neurogenesis, Radiat Res, 162 (2004) 39-47.

Reed et al., Potentiation of melphalan-induced cytotoxicity through targeting of the base excision repair pathway in 42 multiple myeloma, Blood, American Society of Hematolgy, US, vol. 110, No. 11, Part 2, p. 372B.

Richardson et al., Cellular mechanisms of neurogenic inflammation, The Journal of pharmacology and experimental therapeutics, vol. 302 (2002) pp. 839-845.

Robertson et al., Altered expression of Ape1/ref-1 in germ cell tumors and overexpression in NT2 cells confers resistance to bleomycin and radiation. Cancer research, vol. 61, No. 5 (2001) pp. 2220-2225.

Rogakou et al., DNA double-stranded breaks induce histone H2AX phosphorylation on serine 139, The Journal of biological chemistry, vol. 273 (1998) pp. 5858-5868.

Saitou et al., Augmentation of tumor necrosis factor family-induced apoptosis by E3330 in human hepatocellular carcinoma cell lines via inhibition of NFkB, World J Gastroenterol 2005, vol. 11, No. 40, pp. 6258-6261.

Salmon-Chemin et al., 2- and 3-Substituted 1,4-Naphthoquinone Derivatives as Subversive Substrates of Trypanothione Reductase and Lipoamide Dehydrogenase from Trypanosoma cruzi; Synthesis and Correlation between Redox Cycling Activities and in Vitro Cytotoxicity, Journal of Medicinal Chemistry, American Chemical Society, US, vol. 1, 44, No. 4, 2001, pp. 548-565.

Sanchez, et al., Alterations in glutamate uptake in NT2-derived neurons and astrocytes after exposure to gamma radiation, Radiat Res, 171 (2009) 41-52.

Schwab et al., Encyclopedia of Cancer, 2011.

Scott et al., Base excision repair of oxidative DNA damage and association with cancer and aging, Carcinogenesis, vol. 30 (2009) pp. 2-2.

Smith et al., Impaired cutaneous wound healing after sensory denervation in developing rats: effects on cell proliferation and apoptosis, Cell Tissue Res, vol. 307 (2002) pp. 281-291.

Stetler et al., APE1/Ref-1 facilitates recovery of gray and white matter and neurological function after mild stroke injury; PNAS; 2010, vol. 107, No. 7.

Su et al., Interactions of APEI with a redox inhibitor: Evidence for an alternate conformation of the enzyme, Biochemistry Submitted (2010).

Susman E., AACR: All Cancer Therapies May Impair Memory, in: Med Page Today, 2010.

Tatsuoka et al., Preparation and pharmacological evaluation of 4-(1,4-benzoquinon-2-yl)-4-phenylbulanamides as 15 potential cerebral protective agents, Chemical and Pharmaceutical Bulletin, Pharmaceutical Society of Japan, JP, vol. 1, 40, No. 9, Jan. 1, 1992, pp. 2382-2386.

Tell et al., The Many Functions of APEI/Ref-1: Not Only a DNA Repair Enzyme, Antioxid Redox Signal, vol. 11 (2009) pp. 601-620.

Tell et al., The intracellular localization of APE1/Ref-1: more than a passive phenomenon?; Antioxid Redox Signal, vol. 7 (2005) pp. 367-384.

Thompson et al., Histology-specific expression of a DNA repair protein in pediatric rhabdomyosarcomas. Journal of pediatric hematology/oncology vol. 23, No. 4 (2001 ) pp. 234-239.

Tikka et al., Tetracycline derivatives and ceftriaxone, a cephalosporin antibiotic, protect neurons against apoptosis induced by ionizing radiation, J Neurochem, 78 (2001) 1409-1414.

Tmovec et al., Effects of ionizing radiation on the blood brain barrier permeability to pharmacologically active substances, Int J Radial Oncol Biol Phys, 1990, 19, 1581-1587.

Tong et al., Radiation-induced apoptosis in dorsal root ganglion neurons, J Neurocytol, vol. 26 (1997) pp. 771-777.

Tzu-Shean et al., Effects of highly active novel artemisininchloroquinoline hybrid compounds on -hematin formation, parasite morphology and endocytosis in, Biochemical Pharmacology, vol. 82, No. 3, 2001, pp. 236-247.

Van Noort et al., Cell Biology of Autoimmune Diseases, International Rev. of Cytology, 1998, vol. 178, pp. 127-206.

Vascotto et al., Genome-wide analysis and proteomic studies reveal APEI/Ref-1 multifunctional role in mammalian cells, Proteomics, vol. 9 (2009) pp. 1058-1074.

Vasko et al., The repair functionof the multifunctional DNA repair/redox protein APE1 is neuroprotective after ionizing adiation, DNA Repair vol. 10 (2011) pp. 942-952.

Vasko et al., The multifunctional DNA repair/redox enzyme Ape1/Ref-I promotes survival of neurons after oxidative stress, DNA Repair (Arnst), 4 (2005) 367-379.

Wang et al., Neuroimmune interactions: potential target for mitigating or treating intestinal radiation injury, Br J Radial, 80 Spec No. 1 (2007) pp. S41-S48.

Wang et al., Regulation of early and delayed radiation responses in rat small intestine by capsaicin-sensitive nerves, Int J Radiat Oncol Biol Phys, vol. 64 (2006) pp. 1528-1536.

Wilson et al., Base excision repair and the central nervous system, Neuroscience, vol. 145 (2007) pp. 1187-1200.

Wong et al., Mechanisms Of Radiation Injury To The Cenlral Nervous System: Implications For Neuroprotection, Molecular interventions, 4 (2004) 273-284.

Yabunaka et al., Hybrid ubiquinone: novel inhibitor of mitochondrial complex III, Biochimica et Biophysica Acta, Bioenergetics, Armsterdam, NL, vol. 1556, No. 2-3, 2002, pp. 6-112.

(56) References Cited

OTHER PUBLICATIONS

Tamada et al., Cleavage at 5-methylcytosine in DNA by pholosensitized oxidation with 2-methyl-1,4-naphlhoquinone tethered oligodeoxynucleolides, Bioorganic & Medicinal Chemistry Letters, 2005, vol. 15, pp. 665-668.

Ziel et al., Ref-1/Ape is critical for folTTalion of the hypoxia-inducible transcriptional complex on the 25 hypoxic response element of the rat pulmonary artery endothelial cell VEGF gene. The FASEB journal vol. 18, No. 9 (2004) pp. 986-988.

Zou et al., ApeI regulates hematopoietic differentiation of embryonic stem cells through its redox functional domain, Blood, vol. 109 (2007) pp. 1917-1922.

Zou et al., Small-molecule inhibitor of the AP endonuclease 1/REF-1 E3330 inhibits pancreatic cancer cell growth and migration; Mol. Cancer Ter, 2008, vol. 7, No. 7.

\* cited by examiner

COMPOUNDS, COMPOSITIONS AND METHODS FOR TREATING OXIDATIVE DNA DAMAGE DISORDERS

CROSS-REFERENCE TO RELATED APPLICATIONS

This application is a continuation of U.S. patent application Ser. No. 16/416,518, filed May 20, 2019, which is a divisional of U.S. patent application Ser. No. 15/411,450, filed Jan. 20, 2017, which is a continuation of U.S. patent application Ser. No. 15/011,016, filed Jan. 29, 2016, which is a continuation of U.S. patent application Ser. No. 14/122,313, filed Nov. 26, 2013, which is a U.S. national counterpart application of international application No. PCT/US2012/040515 filed Jun. 1, 2012, which claims priority under 35 U.S.C 119(e) to U.S. Provisional Patent Application Ser. No. 61/493,169, filed Jun. 3, 2011, the disclosures of which are each expressly incorporated by reference in their entirety.

STATEMENT OF GOVERNMENT SUPPORT

This invention was made with government support under CA121168 awarded by National Institutes of Health. The government has certain rights in the invention.

TECHNICAL FIELD

The present invention relates to compounds, compositions and formulations useful for treating disorders arising from oxidative DNA damage, including oxidative DNA damage resulting from ionizing radiation or other therapy.

BACKGROUND AND SUMMARY OF THE INVENTION

Evidence in patients and in animal models demonstrates that cancer therapies are often accompanied by neurological side effects. Two major neurological side effects are cognitive dysfunction, also referred to as "chemobrain," and chemotherapy-induced peripheral neuropathy (CIPN). Two such therapies that cause neurological side effects include ionizing radiation and drugs that act through mechanisms causing DNA damage, such as platinum-containing drugs, taxanes, and the like. To date, the cellular mechanisms for cognitive dysfunction or CIPN have not been identified. Furthermore, there are no standard and effective treatments available to prevent or reverse such therapy-induced neurotoxicity.

It has been reported that ionizing radiation (IR) may affect the central nervous system (CNS) secondary to actions on non-neuronal targets such as disruption of the blood-brain barrier[1] or could directly have cytotoxic consequences on neurons[2,3] or neurogenesis[4,5]. It has also been reported that IR can produce significant neurotoxicity, especially upon direct exposure to central nervous system tissues[6,7]. Toxicities have been reported to range from fatigue to cognitive dysfunction[6,8], and, with high exposure, cell loss can occur in the brain and spinal cord[7].

Although many IR neurotoxicity studies focus on the CNS, such radiation therapy may also cause significant toxicity to peripheral neurons (autonomic, motor, or sensory neurons). For example, in the GI tract and bladder, it has been reported that IR alters levels of substance P and calcitonin gene-related peptide (CGRP), two neuropeptides found in small-diameter sensory neurons[9-11]. Reduced capsaicin-evoked CGRP release from sensory neurons has been attributed to indicate reduced sensory neuron functioning. It has also been reported that these peptides modulate intestinal injury after radiation. In particular, CGRP is protective of the tissue, whereas SP contributes to the pathophysiology[12] in the gut, and worsens early-onset radiation-induced toxicity[12].

Using cultured neurons isolated from the central nervous system, several investigators have reported that IR exposure increases production of reactive oxygen species (ROS)[13], produces DNA damage[13,14], and often causes apoptosis [13,15], all in a dose-dependent manner. However, the mechanisms by which IR produces neurotoxicity remain undetermined. Without being bound by theory, it is believed herein that radiation might directly affect sensory neurons, exacerbating radiation-induced injury in various organs. Further, but without being bound by theory, it is believed herein that, in situ, radiation-induced oxidative damage to DNA may subsequently alter neuronal function and cause cell death. There is a need for protecting patients from and/or treating patients with neuronal damage, which may heighten the quality of life, especially of cancer survivors[6,23,24].

It has been discovered herein that modulating the expression of APE1 alters many forms of neurotoxicity, including IR-induced neurotoxicity. It has been observed herein that modulation of DNA repair mechanisms may reverse the undesired neurotoxic effects arising from a number of sources, including a number of anticancer drugs. Without being bound by theory it is believed herein that enhancing the base excision repair pathway may attenuate neuronal damage, such as by chemotherapeutic agents both during and after cancer therapy.

In one embodiment, compounds, compositions, methods, and uses are described herein for treating neurotoxicity. It is demonstrated herein that APE1 is involved in protecting neuronal cells, such as dorsal root ganglion (DRG) cells and hippocampal cells, from toxicity and/or neuronal dysfunction induced by chemotherapy, such as IR and cancer drugs, including platinum-containing drugs, taxanes, and the like. In another embodiment, compounds, compositions, methods, and uses are described herein that include inhibitors of APE1, including small-molecule inhibitors. In one aspect, the inhibitors selectively modulate the redox function of APE1. It has been unexpectedly discovered that negative modulation of the redox function of APE1, irrespective of the modulation of the DNA repair function, enhances neuroprotective activity and is an efficacious therapy for preventing, treating, and/or reversing neuronal damage.

In one embodiment, the compounds, compositions, methods, and uses include one or more compounds of formula (I)

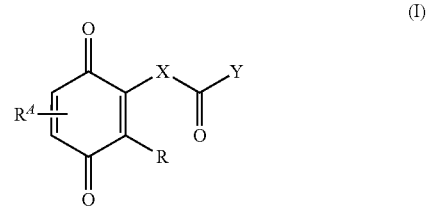

and/or one or pharmaceutically acceptable salts thereof, wherein:

$R^A$ represents two substituents each independently selected from hydrogen, alkoxy, where $R^A$ are not both hydrogen; or $R^A$ represents a fused aryl ring that is optionally substituted;

R is hydrogen or halo, or alkyl, heteroalkyl cycloalkyl, cycloheteroalkyl, alkoxy, heteroalkoxy cycloalkoxy, cycloheteroalkoxy, alkylthio, heteroalkylthio cycloalkylthio, or cycloheteroalkylthio, each of which is optionally substituted;

R is hydrogen or halo, or alkyl, heteroalkyl, cycloalkyl, or cycloheteroalkyl each of which is optionally substituted;

X is alkylene, alkenylene, or alkynylene, each of which is optionally substituted; and X is alkylene or alkenylene, alkynylene, each of which is optionally substituted; and Y forms a carboxylic acid, ester, or amide.

DETAILED DESCRIPTION

Figure 1A:
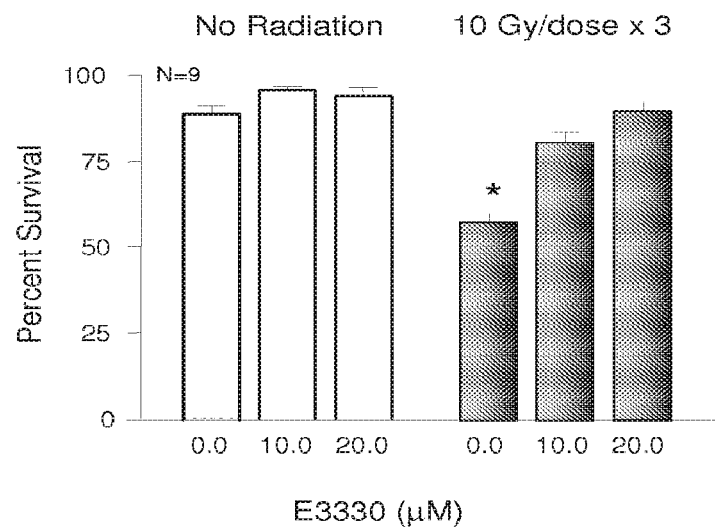
FIG. 1(A) shows the effect of E3330 on cell survival following IR treatment.

It has been reported that compounds of formula (I), including E3330, also referred to as APX3330, are toxic to abnormally dividing cells, such as tumor and cancer cells. However, it has been discovered herein that compounds of formula (I), including E3330, are nontoxic to normally dividing cells, such as epithelial cells and bone marrow cells. It has also been discovered that compounds of formula (I), including E3330, are nontoxic to neuronal cells, including dorsal root ganglion (DRG) cells and hippocampal cells. It has also been discovered that compounds of formula (I), including E3330, are neuroprotective of neuronal cells, and are useful in treating neuronal cell injury. It has also been discovered that compounds of formula (I), including E3330, are useful in treating peripheral neuropathy. Compounds of formula (I), including E3330, are selective inhibitors of the redox function of APE1. It has been discovered herein that the redox function of APE1 is not necessary for either neuronal protection nor the treatment of neuronal injury. Without being bound by theory, it is believed herein that compounds of formula (I), including E3330, enhance the repair function of APE1, a heretofore unknown capability.

Several illustrative embodiments of the invention are described by the following enumerated clauses:

1. A method for preventing or treating neuronal damage in a host animal, the method comprising the step of administering to the host animal a therapeutically effective amount of a compound of the formula

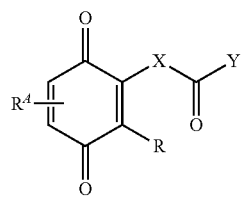

or a pharmaceutically acceptable salt thereof, wherein:

$R^A$ represents two substituents each independently selected from hydrogen, alkoxy, where $R^A$ are not both hydrogen; or $R^A$ represents a fused aryl ring that is optionally substituted;

R is hydrogen or halo, or alkyl, heteroalkyl cycloalkyl, cycloheteroalkyl, alkoxy, heteroalkoxy cycloalkoxy, cycloheteroalkoxy, alkylthio, heteroalkylthio cycloalkylthio, or cycloheteroalkylthio, each of which is optionally substituted; or R is halo, or alkyl or heteroalkyl each of which is optionally substituted X is alkylene, alkenylene, or alkynylene, each of which is optionally substituted; and Y forms a carboxylic acid, ester, or amide.

2. The method of clause 1 wherein each $R^A$ is alkoxy.

3. The method of clause 1 or 2 wherein each $R^A$ is methoxy.

4. The method of clause 1 wherein $R^A$ represents optionally substituted benzo.

5. The method of clause 1 or 4 wherein $R^A$ represents benzo.

6. The method as in any one of the preceding clauses wherein R is hydrogen or halo, or alkyl, heteroalkyl cycloalkyl, or cycloheteroalkyl each of which is optionally substituted;

7. The method of any one of the preceding clauses wherein R is alkyl or heteroalkyl, each of which is optionally substituted.

8. The method of any one of the preceding clauses wherein R is optionally substituted alkyl.

9. The method of any one of the preceding clauses wherein R is alkyl.

10. The method as in any one of the preceding clauses wherein R is methyl.

11. The method any one of clauses 1 to 5 wherein R is alkoxy.

12. The method as in any one of clauses 1 to 5 or 11 wherein R is methoxy.

13. The method of any one of clauses 1 to 5 wherein R is alkylthio.

14. The method of any one of clauses 1 to 5 or 13 wherein R is methylthio.

15. The method as in any one of clauses 1 to 5 wherein R is halo.

16. The method of any one of the preceding clauses wherein X is optionally substituted alkylene.

17. The method of any one of the preceding clauses wherein X is an epoxy alkylene.

18. The method of any one of the preceding clauses wherein X is optionally substituted alkenylene.

19. The method of any one of the preceding clauses wherein X is alkyl substituted alkenylene.

20. The method as in any one of the preceding clauses wherein X is optionally substituted (E)-alkenylene.

21. The method as in any one of the preceding clauses wherein X is alkyl substituted (E)-alkenylene.

22. The method as in any one of the preceding clauses wherein X is alkyl substituted ethenylene.

23. The method as in any one of the preceding clauses wherein X is CHCR$^X$, and R$^X$ is $C_1$-$C_{10}$ alkyl.

24. The method as in any one of the preceding clauses wherein R$^X$ is $C_1$-$C_9$ alkyl.

25. The method as in any one of the preceding clauses wherein R$^X$ is $C_9$ alkyl.

26. The method as in any one of the preceding clauses wherein R$^X$ is n-nonyl.

27. The method as in any one of the preceding clauses wherein $R^X$ is $C_1$-$C_6$ alkyl.

28. The method as in any one of the preceding clauses wherein $R^X$ is $C_1$-$C_4$ alkyl.

29. The method as in any one of the preceding clauses wherein $R^X$ is $C_3$-$C_4$ alkyl.

30. The method as in any one of the preceding clauses wherein $R^X$ is methyl.

31. The method of any one of the preceding clauses wherein Y is OH.

32. The method of any one of the preceding clauses wherein Y forms an ester.

33. The method of any one of the preceding clauses wherein Y forms an alkyl ester.

34. The method of any one clauses 1 to 30 wherein Y forms an amide.

35. The method of any one of clauses 1 to 30 or 34 clauses wherein Y is $N(R^1)_2$ or $NR^2OR^2$, where each $R^1$ is independently selected from the group consisting of alkyl heteroalkyl, cycloalkyl, and cycloheteroalkyl, each of which is optionally substituted, or both $R^1$ are taken together with the attached nitrogen to form an optionally substituted heterocycle; where each $R^2$ is independently selected from the group consisting of hydrogen, alkyl heteroalkyl, cycloalkyl, and cycloheteroalkyl, each of which is optionally substituted, and a prodrug group, or both $R^2$ are taken together with the attached nitrogen and oxygen to form an optionally substituted heterocycle.

36. The method of any one of clauses 1 to 30 or 34 to 35 wherein Y is $N(R^1)_2$ where each $R^1$ is independently selected from the group consisting of hydrogen, alkyl heteroalkyl, cycloalkyl, and cycloheteroalkyl, each of which is optionally substituted, or both $R^1$ are taken together with the attached nitrogen to form an optionally substituted heterocycle.

37. The method as in any one of clauses 1 to 30 or 34 to 36 wherein one $R^1$ is ethyl.

38. The method as in any one of clauses 1 to 30 or 34 to 37 wherein one $R^1$ is methyl.

39. The method of clauses 1 to 30 or 34 to 38 wherein one $R^1$ is optionally substituted alkyl; or each $R^1$ is optionally substituted alkyl.

40. The method of any one of clauses 1 to 30 or 34 to 39 wherein one $R^1$ is alkyl; or wherein each $R^1$ is alkyl.

41. The method as in any one of clauses 1 to 30, 34 to 37, or 39 to 40 wherein each $R^1$ is ethyl.

42. The method as in any one of clauses 1 to 30, 34 to 37, or 39 to 40 wherein each $R^1$ is methyl.

43. The method of any one of clauses 1 to 30 or 34 to 39 wherein at least one $R^1$ is hydroxyalkyl.

44. The method as in any one of clauses 1 to 30, 34 to 39, or 43 wherein one $R^1$ is hydroxyalkyl.

45. The method of any one of clauses 1 to 30 or 34 to 39 wherein at least one $R^1$ is polyhydroxyalkyl.

46. The method as in any one of clauses 1 to 30, 34 to 39, or 45 wherein one $R^1$ is polyhydroxyalkyl.

47. The method as in any one of clauses 1 to 30, 34 to 39, 45, or 46 wherein one $R^1$ is pentahydroxyhexyl.

48. The method as in any one of clauses 1 to 30 or 34 to 36 wherein both $R^1$ are taken together with the attached nitrogen to form an optionally substituted heterocycle selected from the group consisting of pyrrolidine, piperidine, piperazine, morpholine, pyrrolidinone, piperidinone, piperazinone, and morpholinone.

49. The method as in any one of clauses 1 to 30, 34 to 36, or 48 wherein both $R^1$ are taken together with the attached nitrogen to form an alkyl substituted heterocycle selected from the group consisting of pyrrolidine, piperidine, piperazine, morpholine, pyrrolidinone, piperidinone, and piperazinone.

50. The method of any one of clauses 1 to 30, 34 to 36, 48, or 49 wherein both $R^1$ are taken together with the attached nitrogen to form an optionally substituted heterocycle selected from the group consisting of pyrrolidine, piperidine, piperazine, and morpholine.

51. The method as in any one of clauses 1 to 30, 34 to 36, 48, or 49 wherein both $R^1$ are taken together with the attached nitrogen to form an optionally substituted heterocycle selected from the group consisting of piperidine, piperazine, morpholine, and piperidinone.

52. The method as in any one of clauses 1 to 30, 34 to 36, or 48 to 51 wherein both $R^1$ are taken together with the attached nitrogen to form an alkyl substituted piperazine.

53. The method of any one clauses 1 to 30 wherein Y is $NR^2OR^2$, where each $R^2$ is independently selected from the group consisting of hydrogen, alkyl heteroalkyl, cycloalkyl, and cycloheteroalkyl, each of which is optionally substituted, and a prodrug group, or both $R^2$ are taken together with the attached nitrogen and oxygen to form an optionally substituted heterocycle.

54. The method of any one clauses 1 to 30, or 53 wherein at least one $R^2$ is hydrogen.

55. The method of any one clauses 1 to 30, 53, or 54 wherein at least one $R^2$ is optionally substituted alkyl.

56. The method of any one clauses 1 to 30, or 53 to 55 wherein at least one $R^2$ is alkyl.

57. The method as in any one clauses 1 to 30, or 53 to 56 wherein at both $R^2$ are alkyl.

58. The method as in any one clauses 1 to 30, or 53 to 57 wherein at both $R^2$ are methyl.

59. The method as in any one clauses 1 to 30, or 53 wherein both $R^2$ are taken together with the attached nitrogen and oxygen to form an optionally substituted heterocycle selected from the group consisting of oxazolidine, oxazine, oxazapine, oxazolidinone, oxazinone, and oxazapinone.

60. The method of any clauses 1 to 30, 53, or 55 wherein both $R^2$ are taken together with the attached nitrogen and oxygen to form an optionally substituted heterocycle selected from the group consisting of oxazolidine, oxazine, and oxazapine.

61. The method of any one of the preceding clauses wherein the neuronal damage is peripheral neuropathy.

62. The method of any one of the preceding clauses wherein the neuronal damage is in the central nervous system.

63. The method of any one of the preceding clauses wherein the neuronal damage causes or aggravates cognitive dysfunction.

64. The method of any one of the preceding clauses wherein the compound is E3330.

65. The method of any one of clause 1 to 63 wherein the compound is not E3330.

66. The method of any one of the preceding clauses wherein the neuronal damage results at least in part from a disease therapy.

67. The method of any one of the preceding clauses wherein the disease therapy is ionizing radiation.

68. The method of any one of the preceding clauses wherein the disease therapy is cancer therapy.

69. The method of any one of clauses 1 to 66, or 68 wherein the disease therapy is the administration of a platinum-containing drug.

70. The method of any one of clauses 1 to 66, 68, or 69 wherein the disease therapy is the administration of carboplatin, oxoplatin, or a combination thereof.

71. The method of any one of clauses 1 to 68 wherein the disease therapy does not include the administration of a platinum-containing drug.

72. The method of any one of clauses 1 to 68 wherein the disease therapy does not include the administration of cisplatin.

73. The method of any one of clauses 1 to 66, or 68 wherein the disease therapy is the administration of a taxane.

74. The method of any one of clauses 1 to 66, 68, or 73 wherein the disease therapy is the administration of a paclitaxel.

75. A method for preventing or treating a disease mediated by iCGRP release inhibition, the method comprising the step of administering a therapeutically effective amount of the compound of any one of clauses 1 to 65.

76. Use of a compound of any one of clauses 1 to 65 in the manufacture of a medicament for preventing or treating neuronal damage in a host animal.

77. The method or use of any one of the preceding clauses wherein the host animal is a human.

78. The method or use of any one of the preceding clauses wherein the compound is included in a pharmaceutical composition, where the pharmaceutical composition comprises one or more carriers, diluents, or excipients, or a combination thereof.

79. The method or use of any one of the preceding clauses wherein the compound is included in a unit dose or unit dosage form, where the unit dose or unit dosage form optionally comprises one or more carriers, diluents, or excipients, or a combination thereof.

In reciting the foregoing collection of clauses, it is to be understood that all possible combinations of features, and all possible subgenera and subcombination are described. For example, it is to be understood that when $R^A$ is limited to alkoxy, R may be limited to alkyl or heteroalkyl, each of which is optionally substituted, or alternatively, to optionally substituted alkyl, or alternatively, to alkylthio, and so forth. Similarly, when X is limited to alkyl substituted ethenylene, $R^X$ may be limited to n-nonyl, or alternatively, to $C_3$-$C_4$ alkyl, or alternatively, to methyl, and so forth. Similarly, when $R^A$ is limited to benzo, X may be limited to alkyl substituted ethenylene, and $R^1$ may be limited to alkyl, or alternatively, X may be limited to alkyl substituted (E)-alkenylene, and $R^1$ may be limited to polyhydroxyalkyl, or alternatively, X may be limited to CHCR$^X$, where $R^X$ is $C_1$-$C_{10}$ alkyl, and $R^1$ may be limited to methyl, and so forth. Other combinations, subgenera and subcombinations are also described by the collection of clauses.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

Illustrative derivatives include, but are not limited to, both those compounds that may be synthetically prepared from the compounds described herein, as well as those compounds that may be prepared in a similar way as those described herein, but differing in the selection of starting materials. It is to be understood that such derivatives may include prodrugs of the compounds described herein, compounds described herein that include one or more protection or protecting groups, including compounds that are used in the preparation of other compounds described herein.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

It is to be understood that the compounds herein may include prodrugs. The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl) but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl and optionally substituted heteroaryl$(C_2-C_{16})$alkanoyl, such as the aryl or heteroaryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The compounds described herein may be prepared using conventional organic synthetic and process chemistry. Illustrative processes are described in PCT international application serial Nos. PCT/US2012/039529 and PCT/US2008/077213, the disclosures of which are incorporated herein by reference.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect, or to a particular organ or tissue system. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative formats for oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. It is to be understood that one or more carriers, one or more diluents, one or more excipients, and combinations of the foregoing may be used in making the pharmaceutical compositions described herein. It is appreciated that the carriers, diluents, and excipients used to prepare the compositions described herein are advantageously GRAS (generally regarded as safe) compounds.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (generally regarded as safe) compounds.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

It is also to be understood herein that the compounds described herein may be administered prophylactically, contemporanesouly, simultaneously, or curatively.

Cisplatin, carboplatin, oxaliplatin, and other platinum-containing drugs, have been observed to induce a decrease in capsaicin-stimulated release of CGRP from sensory neurons. Cisplatin, carboplatin, oxaliplatin, and other platinum-containing drugs, have been reported to cause DNA cross-linking. In addition, reactive oxygen species (ROS) generation has been observed to accompany treatments that include cisplatin, carboplatin, oxaliplatin, and other platinum-containing drugs. Without being bound by theory, it is believed herein that ROS generation may lead to oxidative stress and oxidative DNA damage. It has been discovered herein that the decrease in capsaicin-stimulated release of CGRP induced by platinum-containing drugs and is attenuated by Ape1 overexpression. Further, it has discovered herein that the decrease in capsaicin-stimulated release of CGRP induced by platinum-containing drugs and is attenuated by administration of compounds described herein.

It has been reported that exposure to ionizing radiation (IR) can produce significant neurotoxicity. It has been observed herein that the manipulation of the base excision DNA repair pathway by altering APE1 expression, affects radiation-induced neurotoxicity. It has also been observed herein that cultures of adult hippocampal and sensory neurons, in which IR produces DNA damage as measured by phosphorylation of histone H2A.X, results in dose-dependent cell death. It has also been observed herein that in isolated sensory neurons, radiation decreases the capsaicin-evoked release of the neuropeptide CGRP. It has also been observed herein that reducing APE1 expression in cultured cells may augment IR-induced neurotoxicity, whereas overexpressing APE1 may be neuroprotective. It has also been observed herein that using lentiviral constructs with a neuronal specific promoter that selectively expresses APE1's differential functions in neurons, selective expression of the DNA repair competent (redox inactive) APE1 constructs in sensory neurons may resurrect cell survival and neuronal function, whereas use of DNA-repair deficient (redox active) constructs may not be protective. It has also been observed herein that use of an APE1 redox-specific inhibitor, including E3330 and other compound of formula (I), also facilitates neuronal protection against IR-induced toxicity. It has also been observed herein that the repair function of APE1 may be at least partially responsible for protecting both hippocampal and neuronal cells, illustratively DRG neuronal cells, from IR-induced damage, while the redox activity of APE1 does not appear to be involved.

The effective use of the compounds, compositions, and methods described herein for treating or ameliorating one or more diseases mediated by Ape1 may be based upon animal models, such as murine, canine, porcine, and non-human primate animal models of disease. For example, it is understood that cancer in humans may be characterized by a loss of function, and/or the development of symptoms, each of which may be elicited in animals, such as mice, and other surrogate test animals. In addition, in vitro assays that include one or more cancer cell lines may be used to evaluate the methods of treatment and the pharmaceutical compositions described herein to determine the therapeutically effective amounts described herein.

ILLUSTRATIVE EXAMPLES

The following examples further illustrate specific embodiments of the invention. However, the following examples should not be interpreted in any way to limit the invention.

Abbreviations: APE1, human apurinic/apyrimidinic (AP) endonuclease; BER, base excision repair; CGRP, calcitonin gene-related peptide; CMV, cytomegalovirus; CNS, central nervous system; DRG, dorsal root ganglion; EGFP, enhanced green fluorescent protein; HA, hemagglutinin antibodies; iCGRP, immunoreactive calcitonin gene-related peptide; IR, ionizing radiation; IRES, internal ribosome entry site; Ref-1, redox effector factor 1; ROS, reactive oxygen species; SCsiRNA, scramble siRNA; SP, (neuropeptide) substance P; WT-APE1, wild type APE1.

EXAMPLE. Materials. Tissue culture supplies were obtained from Invitrogen (Carlsbad, Calif.). Normocin was supplied by InvivoGen (San Diego, Calif.). Nerve growth factor was purchased from Harlan Bioproducts for Science, Inc. (Indianapolis, Ind.). Poly-D-lysine, laminin, peripherin monoclonal antibodies, and routine chemicals were obtained from Sigma-Aldrich Inc. (St. Louis, Mo.). Optiprep was obtained from NYCOMED PHARMA AS (Oslo, Norway). Neuroporter® (transfecting agent) was purchased from Gene Therapy Systems (San Diego, Calif.). Mouse monoclonal antihuman APE1 antibodies were obtained from Novus Biologicals (Littleton, Colo.); anti-phospho-H2A.X antibodies were obtained from Upstate Cell Signaling Solutions (Charlottesville, Va.). Goat anti-mouse HRP conjugated IgG secondary antibody was obtained from Zymed Laboratories Inc. (San Francisco, Calif.); actin antibodies were purchased from Thermo (Fremont Calif.). HA rat monoclonal antibodies were obtained from Roche Applied Science (Mannhiem, Germany) Cy3-conjugated donkey anti-mouse IgG antibody, biotin-conjugated donkey anti-rabbit IgG, and Cy3-conjugated streptavidin were obtained from Jackson ImmunoResearch (West Grove, Pa.). E3330 was synthesized as described in the published literature[25, 26]. The Animal Care and Use Committee at Indiana University School of Medicine, Indianapolis, Ind., approved all procedures used in these studies.

EXAMPLE. Cell Cultures. Neuronal cultures were prepared from adult male (150-175 g) Sprague-Dawley rats (Harlan, Indianapolis, Ind.) as described in the published literature[27, 28]. Briefly, hippocampal cells were dissociated using papain and mechanical agitation and separated by gradient centrifugation. The pellet of cells from a discontinuous gradient of Optiprep in L-15 media was washed then resuspended in 1 mL of growth media consisting of Neurobasal Medium supplemented with 0.5 mM L-glutamine, 2% B-27 Supplement minus AO, 50 mg/mL Penicillin-Streptomycin, and 5 ng/mL of Basic Fibroblast Growth Factor (BFGF). Approximately 60,000 cells were plated onto poly-D-lysine and laminin coated plates and grown for 6-14 days in 5% $CO_2$ at 37° C. Growth medium was changed every other day. For sensory neuronal culture, cells were dissociated using collagenase and mechanical dissociation. Approximately 30,000 DRG cells were plated into each well of 12 well culture plates or onto Lab-Tek chamber slides all precoated with poly-D-lysine and laminin. The sensory neurons were maintained in F-12 media supplemented with 10% horse serum, 2 mM glutamine, 100 μg/mL normocin, 50 μg/mL penicillin, 50 μg/mL streptomycin, 50 μM 5-fluoro-2'-deoxyuridine, 150 μM uridine, and 30 ng/mL NGF in 3% $CO_2$ at 37° C. Growth medium was changed every other day and the cells were used after 11-13 days of culture.

EXAMPLE. Assay Methods. Sensory neuronal cultures grown on Lab-Tek microscope chamber slides were processed for immunofluorescence as previously published using a peripherin antibody (1:500) and HA antibody (1:500)[28]. Images were collected in red (peripherin), green (HA), and bright-field modes. A Zeiss LSM offline browser (R4.0: Carl Zeiss Inc.; Thornwood, N.Y.) was used to determine co-localization of peripherin and HA. For trypan blue exculsion, equal volume of 0.4% (w/v) Trypan blue to cell suspension were combined, mixed and scored under phase contrast microscope. Dead cells were those that take up the trypan blue and stain blue, whereas the live cells have yellow nuclei.

For release studies, the sensory neuronal cultures were washed once with HEPES buffer consisting of (in mM) 25 HEPES, 135 NaCl, 3.5 KCl, 2.5 $CaCl_2$, 1 $MgCl_2$, 3.3 D-glucose, and 0.1% bovine serum albumin, pH 7.4 and maintained at 37° C. They were then incubated for successive 10 mM intervals with 0.4 mL of HEPES buffer alone (to measure resting release), with buffer containing 30 nM capsaicin (to measure stimulated release), then with buffer alone (to measure recovery). After each incubation, the buffer was removed and the amount of CGRP in each sample was measured using radioimmunoassay as previously described[29]. After the release experiment, the cells in each well were scraped and sonicated in 0.4 M HCl and an aliquot taken to measure total CGRP content in the cultures using radioimmunoassay. Total content was calculated by adding the total amount released in all incubations to the amount measured in the cells. The release data is calculated as fmol released/well/10 mM or as a % of the total peptide content in the cells[29]. Western blot analysis was performed as described previously[17, 27].

Neurons were transfected with siRNA to APE1 (APE1siRNA), or scramble siRNA (SCsiRNA) and were used as described in the published literature[28].

EXAMPLE. Development of Viral Constructs. Adenoviral constructs containing 1) the CMV promoter, HA-tagged APE1, IRES, and enhanced green fluorescent protein (EGFP); or 2) CMV, IRES, and EGFP were developed as described in the published literature[28]. DNA sequencing confirmed the constructs in the pLenti6-R4R2-V5 plasmid containing α CaM kinase II promoter (WT-, C65-, or 226+177-) APE1-IRES-EGFP.

For adenoviral infection, adult neuronal cells were cultured as described in the absence or presence of siRNA treatment for 7 days, then exposed to adenoviruses (Ad5-IRES-eGFP and Ad5-HA-APE1-IRES-eGFP) at 30 pfu/cell for hippocampal cultures and 150 pfu/cell for sensory neuronal cultures. After 2 days, the virus was removed; then cells were grown in normal media. For lentiviral infections, DRG cells were cultured 5 days before 150 pfu/cell of the lentivirus was added to the media. Two days later, the virus was removed; then cells were grown an additional 5 days in regular media. It has been previously reported that APE1's repair function is neuroprotective against oxidative DNA damage in hippocampal and sensory neuronal cultures[28] and in those studies and the invention described herein, APE1 expression in rat cells was selectively reduced with siRNA and APE1 transgenes that are not affected by the rat siRNA were added back, since it is reported that the human APE1 homolog to rat APE1 has a different nucleic acid sequence at the binding site[28].

EXAMPLE. Ionizing Radiation Treatment. Irradiation of cell cultures was performed using a Gammacell 40 Exactor Irradiator (Nordion International Inc). On the first day that the cells were exposed to IR, the media was changed and the culture plates transported to the irradiator at room temperature. Exposure times vary with dosing since the machine delivers 10 Gy/~16 min. In all experiments, control cultures were transported to the irradiator and kept in the room for the same time but not exposed to IR.

EXAMPLE. Data Analysis. Data were expressed as the mean± the standard error of the mean (SEM) for at least 3 independent experiments from separate harvests. Statistical significance between groups (p<0.05) was determined using ANOVA, followed by the Tukey post-hoc test.

EXAMPLE. Determining whether reducing APE1 expression augments radiation-induced neuronal cell death. Previously published studies were confirmed, showing that IR produces oxidative DNA damage and apoptosis in neurons[31]. When neuronal cultures were exposed to increasing doses of radiation and viability examined 24 h later using trypan blue exclusion, a dose-dependent cytotoxicity in sensory neuronal cultures and hippocampal cultures was observed. The mean % of cells surviving 24 h after exposure to IR as measured by trypan blue exclusion was evaluated.

Survival of sensory neuronal cells cultured in media alone was 97±2% after a 3-Gy dose and 83±2% after a 10-Gy dose, respectively. After exposure to a 60-Gy dose, only 32±3% of cells appeared to have survived. Exposing hippocampal cultures to a 3- or 10-Gy dose resulted in 92±2% and 69±1% of cells excluding trypan blue, respectively; a 30-Gy dose reduced viability to 41±2%.

It was also determined whether reducing APE1 expression in the cultures would alter IR's toxic effects. Exposing neuronal cultures to SCsiRNA did not appear to significantly alter the number of cells that excluded trypan blue in response to IR, compared to cells treated with medium alone.

In contrast, sensory and hippocampal cultures treated with APE1siRNA appeared to demonstrate enhanced cell death after IR. A 10-Gy dose of radiation appeared to significantly reduce cell viability from 83±2% to 64±2% in sensory neuronal cultures and from 69±1% to 46±1% in hippocampal cultures. Reduced APE1 expression appeared to result in survival of only 10±1% of sensory neurons 24 h after exposure to a 60-Gy dose and 8±2% of hippocampal cells after exposure to a 30-Gy dose. APE1 siRNA reduced hippocampal APE1 levels to 5±5% of the level of control SCsiRNA; APE1 siRNA also reduced APE1 to 15±3% in sensory neuronal cultures compared to cultures treated with SCsiRNA. Scramble siRNA did not appear to significantly alter APE1 expression compared to untreated cultures.

EXAMPLE. Determining whether overexpressing APE1 in neuronal cultures protects against radiation-induced cell death. Because reducing APE1 expression in neuronal cultures appears to enhance radiation-induced cell death, it was determined whether overexpressing APE1 may be neuroprotective. Adenoviral constructs containing the CMV promoter, WT-APE1, IRES, and EGFP were used to infect sensory and hippocampal cultures pretreated with either SCsiRNA or APE1siRNA. Cultured cells were exposed to siRNAs on Days 3-5, to virus on Day 7 (for 48 h), to IR on Day 11, and trypan exclusion measured 24 h after radiation. An adenoviral vector containing the EGFP construct was used as a control. Western blot analysis was performed on all cultures using an HA-antibody[28].

Overexpressing APE1 in neuronal cultures appeared to significantly attenuate IR's ability to cause cell death. When sensory neurons treated with SCsiRNA were exposed to a 60-Gy dose of radiation, only 34±2% of cells were viable after 24 h, but overexpressing APE1 after radiation increased cell viability to 69±4%. In radiated cells where APE1 expression was reduced with siRNA treatment, the "add-back" of APE1 via adenoviral infection increased viability from 10±1% to 53±4%. Analogous results were observed in hippocampal cultures: 30 Gy of radiation reduced cell viability to 43±2% and 8±2% in SCsiRNA and APE1siRNA treated cells, respectively. Overexpressing APE1 increased viability to 66±5% in cultures treated with SCsiRNA and to 49±2% in cells treated with APE1siRNA. Therefore, APE1 overexpression appears to be neuroprotective in cells with either reduced or normal complements of APE1. In the absence of IR, reducing or overexpressing APE1 did not alter cell viability. Infection with the viral vector control did not appear to significantly alter cell viability after radiation in cells treated with either SCsiRNA or APE1siRNA.

EXAMPLE. Effect of APE1 on DNA damage induced by ionizing radiation. To assess whether DNA double-strand breaks after IR, histone H2A.X phosphorylation was measured[32]. Neuronal cultures in the absence or presence of APE1 manipulations were exposed to significant, but not maximal, doses of IR that would affect cell viability: 30 Gy for sensory cells and 15 Gy for hippocampal cells. Histone H2A.X phosphorylation was measured using Western blotting 0.5-3 h after IR exposure. In these experiments, pretreating cultures with APE1siRNA for 48 h appeared to significantly reduce the APE1 level to 15±8% of that in the control sensory neuronal cultures and 10±12% of the control in hippocampal cultures; SCsiRNA did not significantly alter APE1 levels.

Without being bound by theory, it is believed herein that the Western blots may illustrate that irradiating sensory neuronal cultures treated with SCsiRNA (100 nM) increases the amount of phospho-H2A.X. However, reducing APE1 expression via APE1siRNA (100 nM) appeared to significantly increase H2A.X phosphorylation. Three h after radiation, the density of the phospho-H2A.X band (normalized to actin) in cultures exposed to SCsiRNA was 2.8±1.0, whereas the band in cells exposed to APE1siRNA was 12±0.9.

Similar results were observed in hippocampal cultures. Irradiating hippocampal cultures treated with SCsiRNA appeared to significantly increase the amount of phospho-H2A.X 30 and 60 min afterward and this was further increased by APE1 knockdown. Without being bound by theory, it is believed herein that these results may demonstrate that neuronal cultures with reduced APE1 have an increase in double-strand breaks after IR treatment, as evidenced by H2A.X phosphorylation.

Additional experiments were performed to overexpress APE1 in the neuronal cultures to determine if adding APE1 back into the cells provides protection against radiation-induced DNA damage. Treatment with the viral vector for 48 h two days after SCsiRNA or APE1siRNA appeared to increase H2A.X phosphorylation in a manner analogous to controls. Three h after radiation, the density of the phosphor-H2A.X band (normalized to actin) in sensory neuronal cultures exposed to SCsiRNA and adenoviral vector was 1.8±0.6, whereas the band in cells exposed to APE1siRNA and vector was 10±0.9. For hippocampal cultures, 60 min after a 15-Gy dose of radiation, the density of the phospho-H2A.X band (normalized to actin) in cultures exposed to SCsiRNA and adenoviral vector was 3.9±1.6, whereas the band in cells exposed to APE1siRNA and vector was 11±1.9.

Exposing neuronal cultures to an adenovirus containing WT APE1 appeared to dramatically attenuate the radiation-induced increase in phospho-H2A.X. In sensory neuronal cultures exposed to APE1siRNA then Ad5-APE1, the density of phospho-H2A.X normalized to actin was 0.9±0.6 and 0.7±0.3 at 1 and 3 h after radiation, respectively. In hippocampal cultures exposed to APE1siRNA then Ad5-APE1, the density of phospho-H2A.X normalized to actin was 1.3±0.4 and 0.2±0.1 at 30 and 60 min after radiation, respectively. Without being bound by theory, it is believed herein that these results, taken with the cell viability data described herein, may demonstrate that reduced APE1 expression in primary neuronal cultures augments IR cytotoxicity, while adding back the missing APE1 protein restores survival and reduces double-strand breaks, demonstrating that APE1 may be intrinsically involved in neuronal cell survival.

EXAMPLE. Determining whether overexpressing APE1 using a neuronal-specific promoter protects sensory neurons against IR-induced cell death. Although the studies described herein may demonstrate that APE1 overexpression in neuronal cultures is neuroprotective, the use of adenoviral constructs with a CMV promoter does not reveal whether APE1's effects are in neurons themselves or the microenvironment (non-neuronal cells). To examine whether APE1 overexpression that is restricted to neurons is protective, lentiviral constructs were developed using a neuronal-specific promoter α CaM kinase II[33]. Initially, it was ascertained whether the expression of WT-APE1 would be restricted to neurons in culture using immunohistochemistry. Double staining with neuronal markers peripherin[34] and HA-tagged APE1 was used. Exposing sensory neurons to lentivirus for 24 h on Day 7 in culture and examining the cells at Day 12 demonstrates significant expression of HA-tagged APE1 in neurons but not in nonneuronal cells.

The expression of APE1 and HA-tagged WT-APE1, C65-APE1 (redox-deficient/DNA repair-proficient)[17, 28] and 226/177-APE1 (redox-proficient/repair-deficient)[17] in the cultures, used in subsequent studies, was also examined. For these studies, cells were exposed to siRNAs for 48 h starting Day 3 in culture and to viral constructs for 2 days starting on Day 5. Experiments were performed on Day 13, and expression was measured at the end of the experiments.

Neurons treated with the control virus containing the α CaM kinase II promoter and EGFP demonstrated APE1 expression, but no HA-tagged protein was detected. However, APE1 expression increased with the APE1 constructs, as it did in the HA-tagged APE1 constructs. Exposing cells to APE1siRNA reduced APE1 expression; but the viral infection increased APE1 levels to control levels. In cells treated with SCsiRNA, viral infection increased APE1 expression approximately three-fold.

A determination was made whether overexpression of APE1 in sensory neurons was protective when cultures were exposed to 10 Gy of radiation daily for three days and cell viability measured 24 h after the last dose. The cell viability of irradiated sensory neuronal cultures treated with SCsiRNA and the lentiviral vector dropped to 71±6 percent. The siRNA and viral treatments in the absence of radiation did not result in significant cell death. Reducing APE1 expression with siRNA significantly reduced cell viability after radiation: from 97±4% in cells not exposed to radiation to 59±4% in cells exposed to three daily doses of 10 Gy. Overexpressing WT-APE1 in sensory neurons attenuated IR's cytotoxic effects: cell viability in neurons treated with SCsiRNA was 90±4% and 87±4% in neurons treated with APE1siRNA.

Selective overexpression of either the repair-competent APE1 mutation (C65-APE1) or the redox-competent mutation (226+177-APE1) was made. In both cases, these mutations also had an HA tag to allow confirmation of over expression. Overexpressing C65-APE1 in sensory neurons mimicked the effects that were observed with WT-APE1. With expression of the repair-competent mutation viability in cultures treated with SCsiRNA after three daily doses of 10 Gy was 88±6%, whereas viability of cells treated with APE1siRNA was 83±3%. This compares favorably to 71±6 and a 59±4% viability of cells in cultures treated with the lentiviral vector and SCsiRNA or APE1siRNA, respectively. In neurons overexpressing 226+177-APE1, radiation reduced cell viability of cultures treated with SCsiRNA to 68±5%. Cultures treated with APE1siRNA demonstrated 58±3% viability which was not significantly different from vector treated cultures after exposure to IR. These results demonstrate that the increased expression levels of APE1's DNA repair component—not its redox component—are the bases of neuroprotection from IR.

EXAMPLE. Effect of APE1 on radiation-induced changes in release of iCGRP from sensory neurons. To characterize the effects of IR and APE1 on an endpoint of sensory neuronal function, we examined resting and capsaicin-evoked release of the neuropeptide, CGRP. For these studies, the initially determined effects of exposing neuronal cultures to single or multiple doses of 10 Gy of IR on the content and release of iCGRP. 24 h after exposing sensory neurons to either one or two once-daily doses of 10 Gy, there was no significant effect on resting or capsaicin-evoked iCGRP release (as measured in fmol released/well of cells/

10 min) or on the total content of CGRP in the cultures. In contrast, exposing the cultures to 10 Gy/day for 3 or 4 days significantly and unexpectedly reduced the capsaicin-evoked iCGRP release. In a similar manner, the total content of iCGRP was not affected by up to 4 doses of 10 Gy given once per day. Exposing cultures to 5 doses considerably reduced iCGRP content. IR had no appreciable effect on resting release of iCGRP from sensory neurons. Based on these results and the fact that multiple doses of radiation are used in therapy, a dose of 10 GY was given daily for 3 days in subsequent studies and release was examined 24 h after the last dose.

Exposing sensory neurons that were pretreated with SCsiRNA (which did not reduce Ape1 expression) and the lentiviral vector to 3 doses of 10 GY resulted in a significant reduction in capsaicin-evoked release of iCGRP from 10.6±0.5% of total iCGRP content for controls to 7.7±0.4% of total iCGRP content. This inhibition in release by IR is analogous to that observed in untreated cells indicating that SCsiRNA and control viral infection do not affect iCGRP release. When cells were pretreated with Ape1siRNA which reduced the expression of Ape1 by approximately 90%, IR significantly reduced capsaicin-evoked release to 6.8±0.5% of total iCGRP content. It was determined whether increasing the expression of Ape1 or Ape1 mutants in sensory neurons could reverse the effects of IR on iCGRP release. Cultures were first treated with siRNAs, infected with viral vectors using the neuronal specific promoter∝CaM kinase II, then exposed to three doses of 10 Gy and release of iCGRP was measured. When cells treated with SCsiRNA or Ape1 siRNA were infected with the virus containing WT-Ape1 or the C65-Ape1, the ability of IR to reduce capsaicin-evoked peptide release was blocked. For example, in cells exposed to Ape1 siRNA, viral vectors containing the WT-Ape1 or C65-Ape1 constructs and radiation, the capsaicin-evoked release was 9.5±0.8 and 10.4±0.8% of total content, respectively. In contrast, overexpressing the repair deficient/redox competent mutant of Ape1, 226+177A-Ape1 had no effect on the ability of radiation to reduce capsaicin-evoked release of iCGRP. In cells treated with SCsiRNA release was 7.8±0.3% of total content, while in cells exposed to Ape1-siRNA release was 6.4±0.4% of total content. The results together demonstrate that the expression level of the repair component of Ape1 and not the redox function is proportional to the reverse in the functional toxicity produced by IR.

EXAMPLE. The compounds described herein unexpectedly lower IR-induced cell death and inhibition of iCGRP release. The APE1 redox-specific inhibitor E3330 [25,26,35] affected radiation-induced neurotoxicity. E3330 was added to the media 3 days prior to the first IR exposure and maintained throughout the 3 days of radiation treatment (10 Gy/day). Cell viability or release studies were performed 24 h after the last dose of radiation. Consistent with earlier studies, when neuronal cultures were exposed to 3 doses of radiation, cell viability was significantly reduced, to 57±2%, as shown in the FIG. 1(A). However, cultures treated with 10 μM E3330, rather than having no effect, unexpectedly demonstrated cell viability of 81±3%. Exposing cultures to 20 μM E3330 effectively blocks IR's effects, as shown in the FIG. 1(A). Neither concentration of E3330 had any effect on cell viability in cultures that were not exposed to radiation.

Figure 1B:
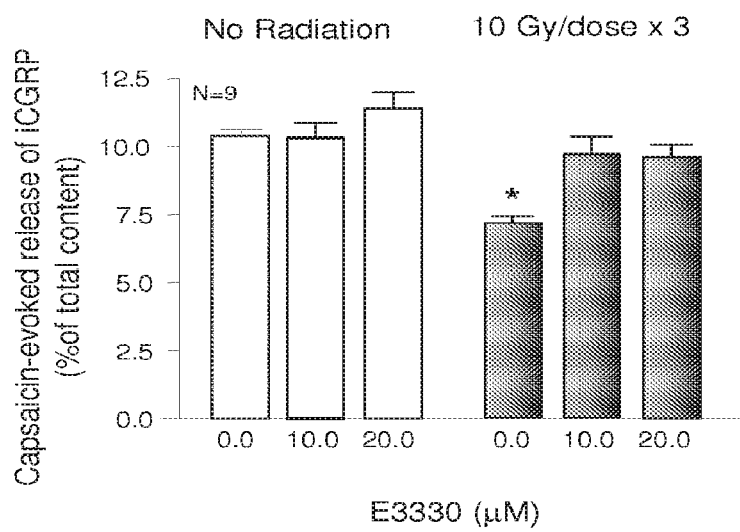
FIG. 1(B) shows the effect of E3330 on capsaicin-evoked iCGRP release following IR treatment.

Release studies also were performed 24 h after the last dose of radiation. 3 doses of 10 Gy significantly reduced capsaicin-evoked iCGRP release from 10.6±0.3% of total iCGRP content in the cultures to 7.1±0.4% of total content, as shown in the following FIG. 1(B). Treating sensory neurons in culture with either 10 μM or 20 μM E3330 completely blocked the effects of radiation on peptide release but did not alter capsaicin-evoked release in control cells. Referring to FIG. 1(A) and FIG. 1(B), E3330 attenuates IR-induced cell death and IR-induced decreases in iCGRP release from sensory neurons. A: Columns represent the mean±SEM of % cells surviving 24 h with no exposure to radiation (open columns) or after exposure to 3 doses of 10 Gy of IR (shaded columns) as measured by trypan blue exclusion. B: Columns show the mean±SEM of the release of iCGRP evoked by 30 nM capsaicin as the % of total iCGRP content over a 10-mM period. Open columns are cultures not exposed to IR; filled columns are cells exposed to 10 Gy/day for 3 days. Cultures were treated with E3330 as indicated for three days before and throughout IR exposure.

Figure 2:
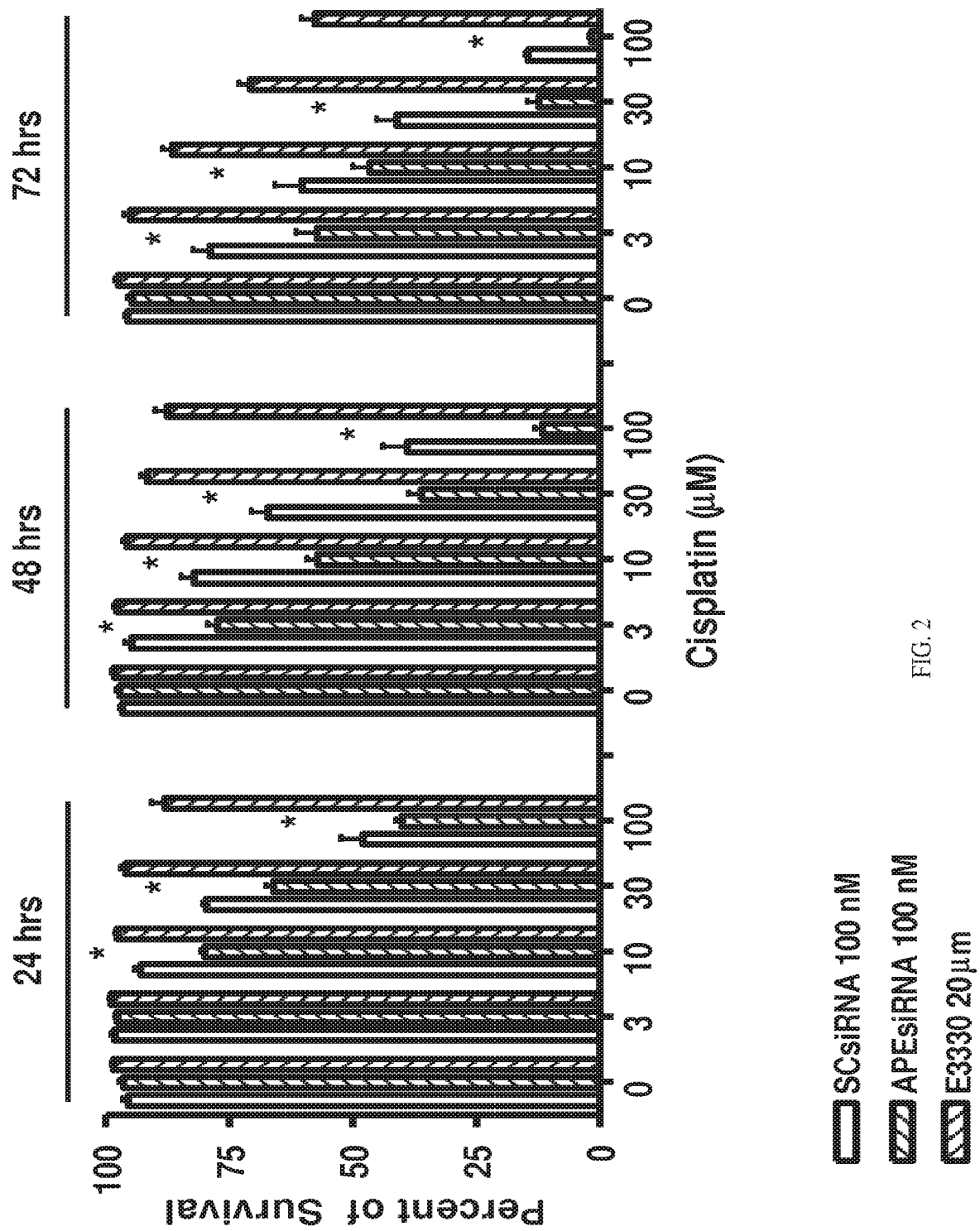
FIG. 2 shows the effect of E3330 on cell survival following cisplatin treatment.

Similarly, the compounds described herein unexpectedly attenuate cell death in cisplatin treated neuronal cells, as shown in FIG. 2 for E3330. Referring to FIG. 2, cells were harvested on day 1. The corresponding siRNA (100 nM) was added on day 3, and removed on day 5. E3330 (20 μM) was dosed on day 7 and remained in the cultures for 2 days. E3330 (20 μM) and/or cisplatin (0-100 mM) are each dosed day 10 with fresh media. Trypan blue assay is performed on days 11, 12, and 13. CGRP release assay is performed on day 11. N=3, *p<0.05.

The compounds described herein, including E3330, reverse the neurotoxicity induced by treatment with IR and platinum-containing drugs. In contrast, E3330 does not attenuate IR-induced cell death and decreases in iCGRP release from sensory neurons that do not express the repair component of APE1, even though E3330 is not active at that function. Without being bound by theory, it is believed herein that the repair component of APE1 is important for neuroprotection. E3330 was tested under conditions of reduced expression of native APE1 coupled with overexpression of the repair deficient/redox competent mutant (266-177-APE1). In these experiments, exposing sensory neuronal cultures to APE1siRNA caused a 84% reduction in native APE1 expression as indicated by Western blotting, whereas viral infection with the 266-177-APE1 construct results in expression of this mutant. Cells were treated with 20 μM E3330 for 3 days prior to the first IR exposure and throughout the 3 days of radiation treatment (10 Gy/day). In contrast to the neuroprotective effects of E3330 in sensory neurons with native APE1, the compound was not effective in cultures overexpressing the APE1 mutant 226-177. Exposing cultures to 10 GY of radiation per day for three days resulted in 75±1% viability in control cells, 56±4% in cells with APE1 knock-down and 53±3% in cells with APE1 knock-down and overexpression of 266-177-APE1. Viability after E3330 was 51±3%. In a similar manner IR reduced the evoked release of iCGRP from 10.7±0.5% of total peptide content to 7.5±0.4% of total content. With APE1 knock-down and 266-177 overexpression release was 5.6±0.2% of total content in the absence of E3330 and 5.9±0.5% with E3330 treatment. Without being bound by theory, it is believed herein that the compounds described herein, including E3330, potentiate the repair component of APE1 even they only have activity at the redox component.

EXAMPLE. CGRP. Release studies were performed on cells. Briefly, neuronal cultures were washed once with HEPES buffer consisting of 25 HEPES, 135 NaCl, 3.5 KCl, 2.5 CaCl2, 1 MgCl2, 3.3 d-glucose (each in mmol/L), and 0.1% bovine serum albumin (pH 7.4), maintained at 37° C., and then incubated for successive 10-min intervals with 0.4 mL of the same buffer in the absence or presence of drugs. Basal or resting release was determined by exposing the cells to HEPES buffer alone, whereas stimulated release was determined by exposing the cultures to 30 nmol/L capsaicin.

Figure 3A:
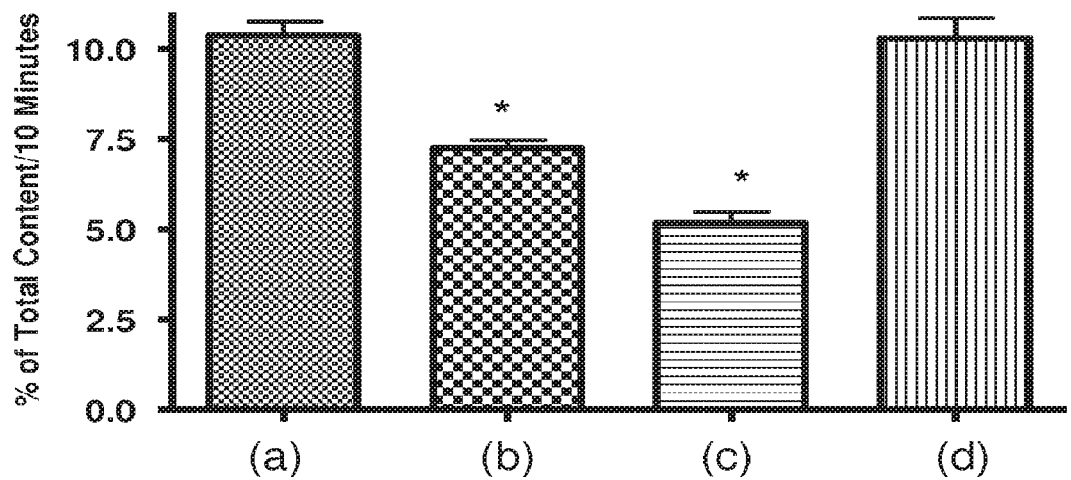
FIG. 3(A) shows the effect of E3330 on % total iCGRP release following cisplatin treatment.

Cells then were reexposed to HEPES buffer without drugs for one or two 10-min incubations to reestablish resting release. During incubations, the cells were maintained in at 37° C. After each incubation, the buffer was removed to measure the amount of CGRP using RIAs. At the end of each release experiment, the cells are scraped and sonicated in 0.4 mol/L HCl and an aliquot was taken to measure total CGRP content in the cultures using RIA. Total content is determined by adding the total amount released in all incubations to the amount remaining in the cells. The release data is calculated as a percentage of the total peptide content in the cells. Because CGRP was measured by RIA, results are expressed as CGRP-like immunoreactivity (iCGRP). FIG. 3 shows the CGRP release from DRG cells, as a percent of total content. Cells are pretreated with a compound described herein, such as E3330 shown in FIG. 3(A), for 3 days, then treated with cisplatin for 24 hours.

Figure 3B:
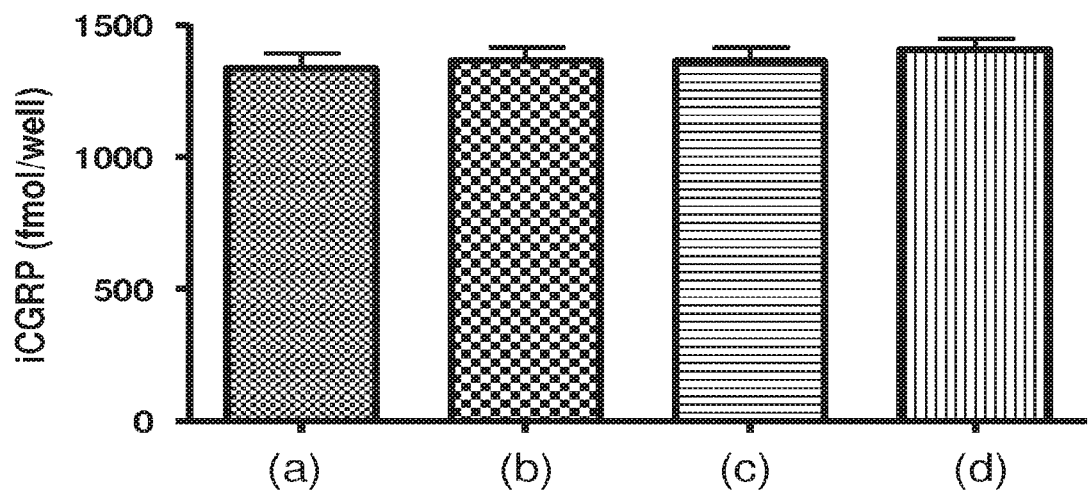
FIG. 3(B) shows the effect of E3330 on total content CGRP following cisplatin treatment.

Referring to FIG. 3(A), N=12, *p<0.05; (a) SCsiRNA; (b) SCsiRNA+ cisplatin (10 μM); (c) APEsiRNA+ cisplatin (10 μM); (d) E3330 (20 μM)+ cisplatin (10 μM). FIG. 3(B) shows the total content CGRP release from DRG cells. Cells are pretreated with a compound described herein, such as E3330 shown in FIG. 3(A), for 3 days, then treated with cisplatin for 24 hours. Referring to FIG. 3 (B), N=12, no statistical significance difference; (a) SCsiRNA; (b) SCsiRNA+ cisplatin (10 μM); (c) APEsiRNA+ cisplatin (10 μM); (d) E3330 (20 μM)+ cisplatin (10 μM).

EXAMPLE. DRG cells are treated with cisplatin (50 μM), with and without co-treatment with E3330 (50 μM), for 3 days. The cells are evaluated by FACS assay and compared to control. The compounds described herein, including E3330, decrease apoptosis arising from cisplatin treatment in DRG cells (n=5, *p<0.05).

EXAMPLE. Cells were pretreated with E3330 (20 μM) for 3 days, then treated with cisplatin (10 μM) for 24 hours. The compounds described herein, including E3330, show recovery of CGRP release from DRG cells: Comparison of (a) SCsiRNA; (b) SCsiRNA+ cisplatin (10 μM); (c) APEsiRNA+ cisplatin (10 μM); (d) E3330 (20 μM)+ cisplatin (10 μM). N=12; *p<0.05 decreased cell function compared to control; *p<0.05 E3330 mediated recovery of cell function compared to cisplatin treatment, and not significantly different from untreated (cisplatin) control. Basal levels of CGRP without induction and cumulative total basal are both monitored, indicating correct functioning of the assay. The iCGRP data show that capsaicin (30 nM) induced CGRP production (a marker of healthy cells) can be recovered from cisplatin treatment by the co-admin of compounds described herein.

EXAMPLE. Animal model of neuropathy, measurement of blood flow in rats. Initial experiments to examine changes in blood flow are performed. Briefly, rats are anesthetized with 100 mg/kg sodium thiopental and the hair on the dorsal hindpaw shaved. The rats are placed on a heated (37° C.) platform to maintain body temperature. Blood flow is measured using a BLF21D laser Doppler flowmeter from Transonic systems Inc. (Ithaca, N.Y.) and a type N 11 G needle-style probe gently placed in contact with the hindpaw using a micromanipulator. This system measures activity of red blood cell flux in 2 mm3 area beneath the probe. Voltage output corresponding to tissue perfusion units (TPUs) is recorded on-line using a Biopac data acquisition system (Goleta, Calif.). Vasodilatation is induced by intradermal injection of capsaicin, methacholine (Sigma Chemical Company, St. Louis, Mo.) or α-CGRP (Bachem). The other hindpaw of the rat receives the vehicle, 0.01% MPL (Aldrich Chemical Co., Milwaukee, Wis.). Injections are made 1 mm away from the probe site by inserting a 27 G needle into the skin at an angle of 15° and the injection volume is 1 μL.

To examine vasodilatation in response to sciatic nerve stimulation, an initial baseline is recorded, after which the sciatic nerve is exposed at the mid-thigh level. To prevent injury-induced action potentials, 1% lidocaine is applied to the proximal end of the sciatic nerve for 2 min. The nerve is cut 2 mm distal to the lidocaine application site and is placed into a nerve cuff fitted with a silver-stimulating electrode. A layer of petroleum jelly is applied over the stimulating electrode, the skin is sutured, and the animal is returned to the heated platform. Baseline blood flow following axotomy is recorded for 30 min to allow sufficient time for the lidocaine block to be extinguished, then a stimulus amplitude of 5 mA at 10 Hz for 30 s is used to induce vasodilatation.

To examine if the stimulation-induced vasodilatation in the hindpaw is mediated by CGRP, 20 μM of the CGRP receptor antagonist, CGRP8-37, is injected 5 mM before application of stimulus. Compounds described herein are efficacious in treating neuropathy.

Figure 4:
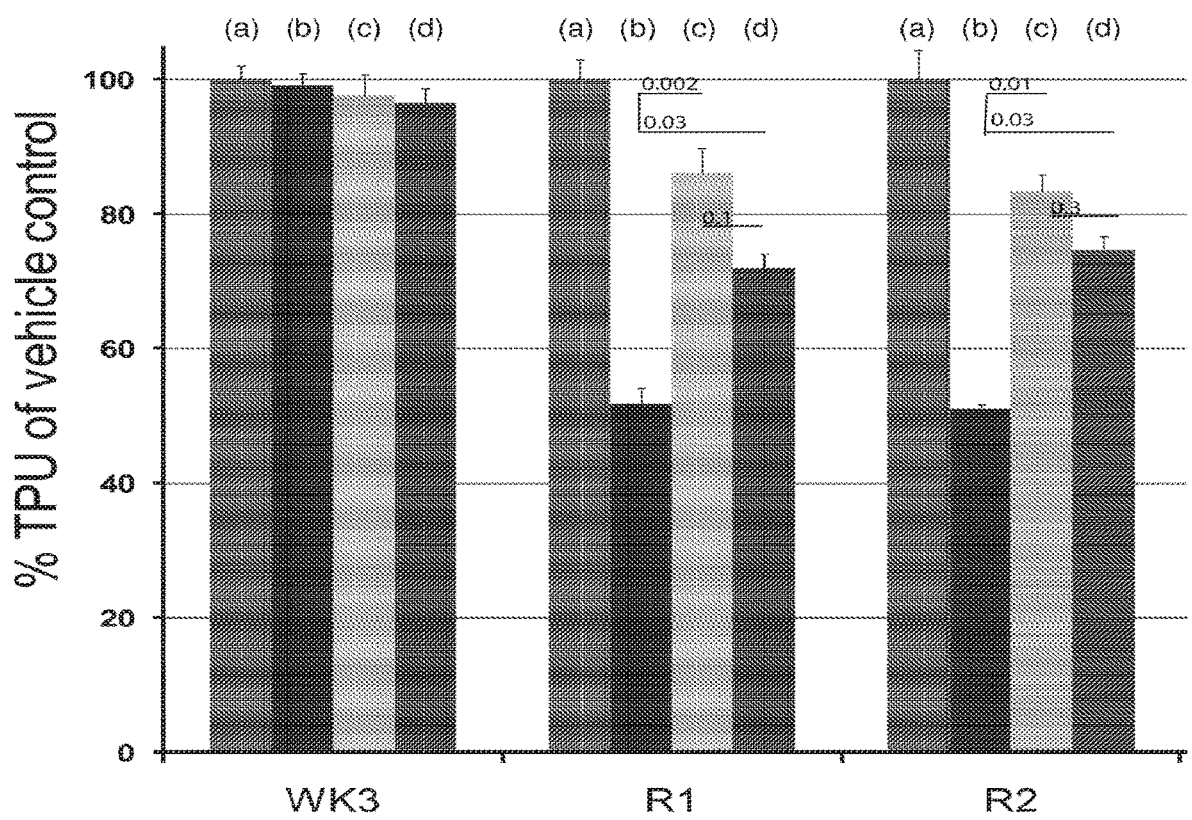
FIG. 4 shows the effect of E3330 on in vivo vasodilation following cisplatin treatment.

Referring to FIG. 4, In vivo vasodilation experiments using cisplatin and E3330, mice were treated with E3330 for 5 days, bid, ip at 25 mg/kg. Cisplatin was administered on day 3. This pattern was repeated for 3 weeks (Wk1, Wk2, Wk3) followed by 3 weeks of recovery with no treatments. At the end of each week (TPU), vasodilation analysis was performed. (a) V=vehicle, (b) V+Cis=cisplatin at 3 mg/kg, (c) E3330+NS=E3330+vehicle, and (d) E3330+Cis3=E3330 plus cisplatin at 3 mg/kg.

EXAMPLE. Redox EMSA Assay. Conventional electrophoresis measuring Ape1 expression with 0.02 mM DTT is used to evaluate test compounds. Additional details are described in Fishel et al. Mol Cancer Ther. 2011 September; 10(9):1698-708 & Luo et al., Antioxid Redox Signal. 2008 November; 10(11):1853-67.

COMPOUND EXAMPLES

The following additional example compounds are described herein. The following compounds inhibit the redox function of APE1 as indicated by EMSA.

| Example | | EMSA (IC$_{50}$) |
|---|---|---|
| 1 | [structure] | 6.2 |

-continued
| Example | | EMSA (IC$_{50}$) |
|---|---|---|
| 2 | 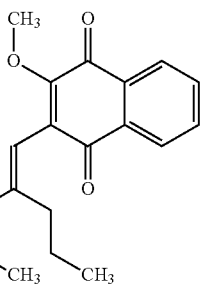 | 2.3 |
| 3 | 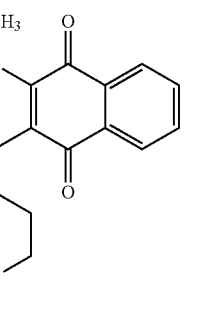 | 3.3 |
| 4 | 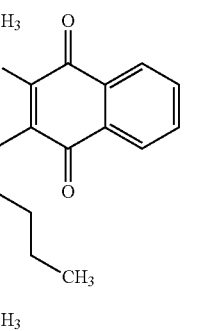 | — |
| 5 | 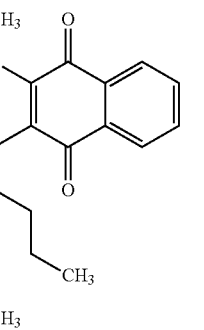 | <1 |

| Example | EMSA (IC$_{50}$) |
|---------|------------------|
| 6 [structure: 2-methyl-1,4-naphthoquinone with =CH-C(=CH-C(=O)-NHCH$_3$)-CH$_2$CH$_2$CH$_2$CH$_3$ substituent] | 17 |
| 7 [structure: 2-methyl-1,4-naphthoquinone with =CH-C(C(=O)-N(CH$_3$)$_2$)-CH$_2$CH$_2$CH$_2$CH$_3$ substituent] | 23 |
| 8 [structure: 2-methyl-1,4-naphthoquinone with =CH-C(C(=O)-NHCH$_2$CH$_3$)-CH$_2$CH$_2$CH$_2$CH$_3$ substituent] | 20 |
| 9 [structure: 2-methyl-1,4-naphthoquinone with =CH-C(C(=O)-N(CH$_2$CH$_3$)$_2$)-CH$_2$CH$_2$CH$_2$CH$_3$ substituent] | 120 |

-continued
| Example | | EMSA (IC$_{50}$) |
|---|---|---|
| 10 | 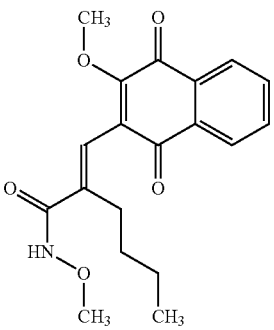 [SMILES: CCCC/C(=C\C1=C(OC)C(=O)c2ccccc2C1=O)C(=O)NOC] | <1 |
| 11 | 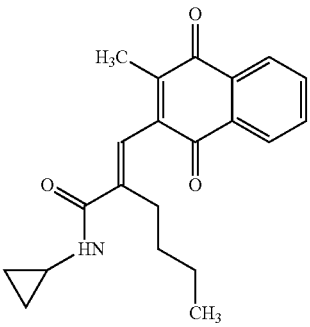 [SMILES: CCCC/C(=C\C1=C(C)C(=O)c2ccccc2C1=O)C(=O)NC1CC1] | 14 |
| 12 | 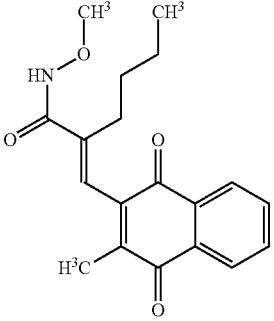 [SMILES: CCCC/C(=C\C1=C([3CH3])C(=O)c2ccccc2C1=O)C(=O)NOC] | — |
| 13 | 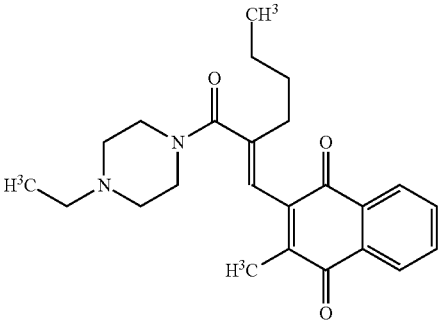 [SMILES: CCCC/C(=C\C1=C([3CH3])C(=O)c2ccccc2C1=O)C(=O)N1CCN(C[3CH3])CC1] | — |

-continued
| Example | | EMSA (IC$_{50}$) |
|---|---|---|
| 14 | 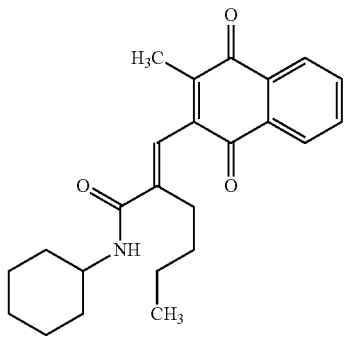 [SMILES: CCCC/C(=C\C1=C(C)C(=O)c2ccccc2C1=O)C(=O)NC1CCCCC1] | 98 |
| 15 | 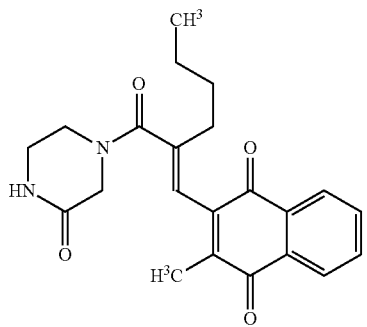 [SMILES: CCCC/C(=C\C1=C([3CH3])C(=O)c2ccccc2C1=O)C(=O)N1CCNC(=O)C1] | 23 |
| 16 | 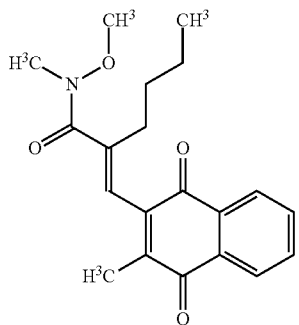 [SMILES: CCCC/C(=C\C1=C([3CH3])C(=O)c2ccccc2C1=O)C(=O)N([3CH3])OC] | 26 |
| 17 | 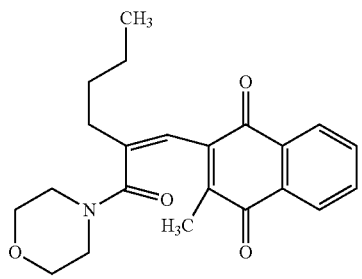 [SMILES: CCCC/C(=C/C1=C(C)C(=O)c2ccccc2C1=O)C(=O)N1CCOCC1] | 25 |

-continued

| Example | | EMSA (IC$_{50}$) |
|---|---|---|
| 18 | [structure: 2-methyl-1,4-naphthoquinone with CH=C(CH2CH2CH2CH3)C(O)-morpholine substituent] | 34 |
| 19 | [structure: 2-methyl-1,4-naphthoquinone with CH=C(CH2CH2CH2CH3)C(O)NH2 substituent] | — |
| 20 | [structure: 2-methyl-1,4-naphthoquinone with CH=C(CH2CH2CH2CH3)C(O)NHCH2CH2OCH3 substituent] | 94 |
| 21 | [structure: 2-methyl-1,4-naphthoquinone with CH=C(CH2CH2CH2CH3)C(O)NHCH2CH2OMe substituent] | 40 |
| 22 | [structure: 2-chloro-1,4-naphthoquinone with CH=C(CH2CH2CH3)C(O)NH-OCH3 substituent] | <2.5 |

-continued

| Example | EMSA (IC$_{50}$) |
|---------|------------------|
| 23      | 2.5              |
| 24      | >10              |
| 25      | 13               |
| 26      | 2.6              |
| 27      | —                |

-continued
| Example | EMSA (IC$_{50}$) |
|---|---|
| 28 (E3330) | 16-29 |
| 29 | 17 |
| 30 | 15 |
| 31 | 24 |
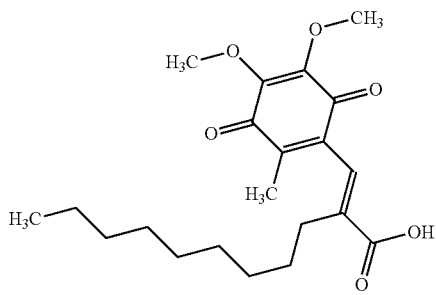 [SMILES: CCCCCCCCC/C(=C\C1=C(C)C(=O)C(OC)=C(OC)C1=O)C(=O)O]
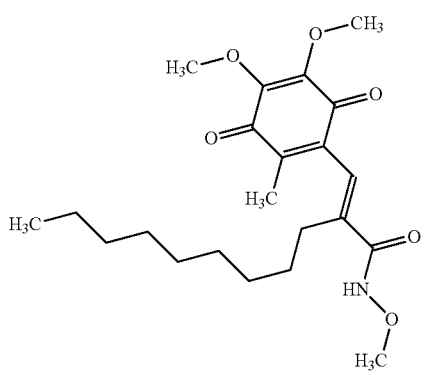 [SMILES: CCCCCCCCC/C(=C\C1=C(C)C(=O)C(OC)=C(OC)C1=O)C(=O)NOC]
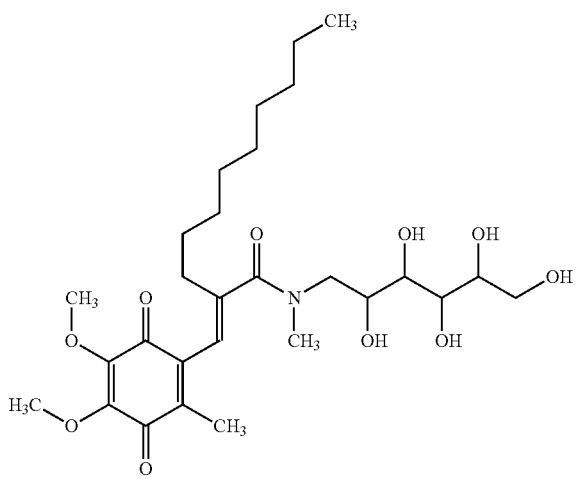 [SMILES: CCCCCCCCC/C(=C\C1=C(C)C(=O)C(OC)=C(OC)C1=O)C(=O)N(C)CC(O)C(O)C(O)C(O)CO]
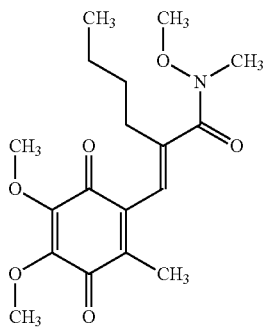 [SMILES: CCCC/C(=C\C1=C(C)C(=O)C(OC)=C(OC)C1=O)C(=O)N(C)OC]

| Example | | EMSA (IC$_{50}$) |
|---|---|---|
| 32 | 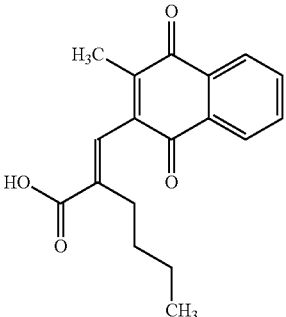 | 47-52 |
| 33 | 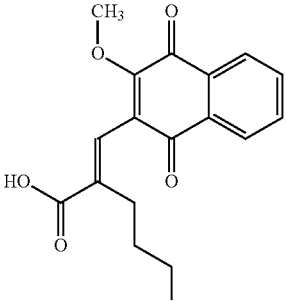 | 0.5 |

The following publications, and each additional publication cited herein, are incorporated herein by reference in their entirety.

[1] T. Trnovec, Z. Kallay, S. Bezek, Effects of ionizing radiation on the blood brain barrier permeability to pharmacologically active substances, Int J Radiat Oncol Biol Phys, 19 (1990) 1581-1587.

[2] M. C. Sanchez, A. Benitez, L. Ortloff, L. M. Green, Alterations in glutamate uptake in NT2-derived neurons and astrocytes after exposure to gamma radiation, Radiat Res, 171 (2009) 41-52.

[3] T. Tikka, T. Usenius, M. Tenhunen, R. Keinanen, J. Koistinaho, Tetracycline derivatives and ceftriaxone, a cephalosporin antibiotic, protect neurons against apoptosis induced by ionizing radiation, J Neurochem, 78 (2001) 1409-1414.

[4] T. M. Madsen, P. E. Kristjansen, T. G. Bolwig, G. Wortwein, Arrested neuronal proliferation and impaired hippocampal function following fractionated brain irradiation in the adult rat, Neuroscience, 119 (2003) 635-642.

[5] J. Raber, R. Rola, A. LeFevour, D. Morhardt, J. Curley, S. Mizumatsu, S. R. VandenBerg, J. R. Fike, Radiation-induced cognitive impairments are associated with changes in indicators of hippocampal neurogenesis, Radiat Res, 162 (2004) 39-47.

[6] J. Dietrich, M. Monje, J. Wefel, C. Meyers, Clinical Patterns and Biological Correlates of Cognitive Dysfunction Associated with Cancer Therapy, Oncologist, 13 (2008) 1285-1295.

[7] C. S. Wong, A. J. Van der Kogel, Mechanisms Of Radiation Injury To The Central Nervous System: Implications For Neuroprotection, Molecular interventions, 4 (2004) 273-284.

[8] F. H. Hochberg, B. Slotnick, Neuropsychologic impairment in astrocytoma survivors, Neurology, 30 (1980) 172-177.

[9] R. Crowe, J. Vale, K. R. Trott, P. Soediono, T. Robson, G. Burnstock, Radiation-induced changes in neuropeptides in the rat urinary bladder, J Urol, 156 (1996) 2062-2066.

[10] U. Hockerfelt, L. Franzen, U. Kjorell, S. Forsgren, Parallel increase in substance P and VIP in rat duodenum in response to irradiation, Peptides, 21 (2000) 271-281.

[11] J. Wang, M. Hauer-Jensen, Neuroimmune interactions: potential target for mitigating or treating intestinal radiation injury, Br J Radiol, 80 Spec No 1 (2007) S41-48.

[12] J. Wang, H. Zheng, A. Kulkarni, X. Ou, M. Hauer-Jensen, Regulation of early and delayed radiation responses in rat small intestine by capsaicin-sensitive nerves, Int J Radiat Oncol Biol Phys, 64 (2006) 1528-1536.

[13] M. Scott, H. S. Shepherd, H. Charlotte, C. d. S.-P. Nadja, A. B. Vilhelm, Base excision repair of oxidative DNA damage and association with cancer and aging, Carcinogenesis, 30 (2009) 2-2.

[14] M. M. Hsieh, V. Hegde, M. R. Kelley, W. A. Deutsch, Activation of APE/Ref-1 redox activity is mediated by reactive oxygen species and PKC phosphorylation, Nucleic Acids Res, 29 (2001) 3116-3122.

[15] J.-P. Belzile, S. A. Choudhury, D. Cournoyer, T. Y. K. Chow, Targeting DNA Repair Proteins: A Promising Avenue for Cancer Gene Therapy, Current Gene Therapy, 6 (2006) 111-123.

[16] M. L. Fishel, M. R. Vasko, M. R. Kelley, DNA repair in neurons: so if they don't divide what's to repair?, Mutation research, 614 (2007) 24-36.

[17] Y. Jiang, C. Guo, M. L. Fishel, Z.-Y. Wang, M. R. Vasko, M. R. Kelley, Role of APE1 in differentiated neuroblastoma SH-SY5Y cells in response to oxidative stress: Use of APE1 small molecule inhibitors to delineate APE1 functions, DNA Repair, 8 (2009) 1273-1282.

[18] M. Luo, H. He, M. R. Kelley, M. Georgiadis, Redox Regulation of DNA Repair: Implications for Human Health and Cancer Therapeutic Development, Antioxid Redox Signal, 12 (2010) 1247-1269.

[19] G. Tell, F. Quadrifoglio, C. Tiribelli, M. R. Kelley, The Many Functions of APE1/Ref-1: Not Only a DNA Repair Enzyme, Antioxid Redox Signal, 11 (2009) 601-620.

[20] A. R. Evans, M. Limp-Foster, M. R. Kelley, Going APE over ref-1, Mutation research, 461 (2000) 83-108.

[21] B. Paap, D. M. Wilson, III, B. M. Sutherland, Human abasic endonuclease action on multilesion abasic clusters: implications for radiation-induced biological damage, Nucl. Acids Res., (2008) gkn118.

[22] D. M. Wilson III, D. R. McNeill, Base excision repair and the central nervous system, Neuroscience, 145 (2007) 1187-1200.

[23] A. Mozes, Cancer Survivors May Be at Risk for Memory Problems, in: Health Day News, 2010.

[24] E. Susman, AACR: All Cancer Therapies May Impair Memory, in: Med Page Today, 2010.

[25] M. R. Kelley, M. Luo, A. Reed, D. Su, S. Delaplane, R. F. Borch, R. L. Nyland II, M. L. Gross, M. Georgiadis, Functional analysis of new and novel analogs of E3330 that block the redox signaling activity of the multifunctional AP endonuclease/redox signaling enzyme APE1/Ref-1, Antioxid Redox Signal (2011).

[26] R. L. Nyland, M. Luo, M. R. Kelley, R. F. Borch, Design and Synthesis of Novel Quinone Inhibitors Targeted to the Redox Function of Apurinic/Apyrimidinic Endonuclease 1/Redox Enhancing Factor-1 (Ape1/Ref-1), Journal of medicinal chemistry, 53 (2010) 1200-1210.

[27] G. J. Brewer, J. R. Torricelli, E. K. Evege, P. J. Price, Optimized survival of hippocampal neurons in B27-supplemented Neurobasal, a new serum-free medium combination, J Neurosci Res, 35 (1993) 567-576.

[28] M. R. Vasko, C. Guo, M. R. Kelley, The multifunctional DNA repair/redox enzyme Ape1/Ref-1 promotes survival of neurons after oxidative stress, DNA Repair (Amst), 4 (2005) 367-379.

[29] Y. Jiang, C. Guo, M. R. Vasko, M. R. Kelley, Implications of Apurinic/Apyrimidinic Endonuclease in Reactive Oxygen Signaling Response after Cisplatin Treatment of Dorsal Root Ganglion Neurons, Cancer Res, 68 (2008) 6425-6434.

[30] J. J. Chen, L. A. Barber, J. Dymshitz, M. R. Vasko, Peptidase inhibitors improve recovery of substance P and calcitonin gene-related peptide release from rat spinal cord slices, Peptides, 17 (1996) 31-37.

[31] J. X. Tong, M. A. Vogelbaum, R. E. Drzymala, K. M. Rich, Radiation-induced apoptosis in dorsal root ganglion neurons, J Neurocytol, 26 (1997) 771-777.

[32] E. P. Rogakou, D. R. Pilch, A. H. Orr, V. S. Ivanova, W. M. Bonner, DNA double-stranded breaks induce histone H2AX phosphorylation on serine 139, The Journal of biological chemistry, 273 (1998) 5858-5868.

[33] K. Mima, S. Deguchi, T. Yamauchi, Characterization of 5' flanking region of alpha isoform of rat Ca2+/calmodulin-dependent protein kinase II gene and neuronal cell type specific promoter activity, Neurosci Lett, 307 (2001) 117-121.

[34] M. E. Goldstein, S. B. House, H. Gainer, NF-L and peripherin immunoreactivities define distinct classes of rat sensory ganglion cells, J Neurosci Res, 30 (1991) 92-104.

[35] M. Hiramoto, N. Shimizu, K. Sugimoto, J. Tang, Y. Kawakami, M. Ito, S. Aizawa, H. Tanaka, I. Makino, H. Handa, Nuclear targeted suppression of NF-kappa B activity by the novel quinone derivative E3330, J Immunol, 160 (1998) 810-819.

[36] G. T. Gobbel, P. H. Chan, Neuronal death is an active, caspase-dependent process after moderate but not severe DNA damage, J Neurochem, 76 (2001) 520-531.

[37] S. A. Gilmore, T. J. Sims, Glial-glial and glial-neuronal interfaces in radiation-induced, glia-depleted spinal cord, J Anat, 190 (Pt 1) (1997) 5-21.

[38] M. R. Kelley, M. L. Fishel, DNA repair proteins as molecular targets for cancer therapeutics, Anticancer Agents Med Chem, 8 (2008) 417-425.

[39] M. Georgiadis, M. Luo, R. Gaur, S. Delaplane, X. Li, M. Kelley, Evolution of the redox function in mammalian Apurinic/apyrimidinic Mutation research, 643 (2008) 54-63.

[40] A. Bapat, L. S. Glass, M. Luo, M. L. Fishel, E. C. Long, M. M. Georgiadis, M. R. Kelley, Novel small molecule inhibitor of Ape1 endonuclease blocks proliferation and reduces viability of glioblastoma cells, J Pharmacol Exp Ther., 334 (2010) 988-998.

[41] D. Su, S. Delaplane, M. Luo, D. Rempel, B. Vu, M. R. Kelley, M. L. Gross, M. Georgiadis, Interactions of APE1 with a redox inhibitor: Evidence for an alternate conformation of the enzyme, Biochemistry Submitted (2010).

[42] D. R. McNeill, D. M. Wilson, 3rd, A Dominant-Negative Form of the Major Human Abasic Endonuclease Enhances Cellular Sensitivity to Laboratory and Clinical DNA-Damaging Agents, Mol Cancer Res, 5 (2007) 61-70.

[43] G. Tell, G. Damante, D. Caldwell, M. R. Kelley, The intracellular localization of APE1/Ref-1: more than a passive phenomenon?, Antioxid Redox Signal, 7 (2005) 367-384.

[44] C. Vascotto, L. Cesaratto, L. A. Zeef, M. Deganuto, C. D'Ambrosio, A. Scaloni, M. Romanello, G. Damante, G. Taglialatela, D. Delneri, M. R. Kelley, S. Mitra, F. Quadrifoglio, G. Tell, Genome-wide analysis and proteomic studies reveal APE1/Ref-1 multifunctional role in mammalian cells, Proteomics, 9 (2009) 1058-1074.

[45] A. Jiang, H. Gao, M. R. Kelley, X. Qiao, Inhibition of APE1/Ref-1 Redox Activity with APX3330 Blocks Retinal Angiogenesis in vitro and in vivo, Vision Res, 51 (2011).

[46] G. M. Zou, M. H. Luo, A. Reed, M. R. Kelley, M. C. Yoder, Ape1 regulates hematopoietic differentiation of embryonic stem cells through its redox functional domain, Blood, 109 (2007) 1917-1922.

[47] P. Holzer, Local effector functions of capsaicin-sensitive sensory nerve endings: involvement of tachykinins, calcitonin gene-related peptide and other neuropeptides, Neuroscience, 24 (1988) 739-768.

[48] J. D. Richardson, M. R. Vasko, Cellular mechanisms of neurogenic inflammation, The Journal of pharmacology and experimental therapeutics, 302 (2002) 839-845.

[49] S. D. Brain, Sensory neuropeptides: their role in inflammation and wound healing, Immunopharmacology, 37 (1997) 133-152.

[50] P. G. Smith, M. Liu, Impaired cutaneous wound healing after sensory denervation in developing rats: effects on cell proliferation and apoptosis, Cell Tissue Res, 307 (2002) 281-291.

What is claimed is:

1. A compound for preventing or treating neuronal damage in a host animal, the compound having the formula

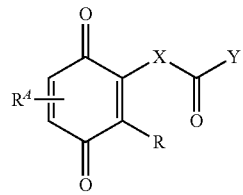

or a pharmaceutically acceptable salt thereof, wherein:
R$^A$ represents a fused aryl ring that is optionally substituted;
R is alkoxy, heteroalkoxy, cycloalkoxy, or cycloheteroalkoxy, each of which is optionally substituted;
X is alkylene, alkenylene, or alkynylene, each of which is optionally substituted; and
Y is N(R$^1$)$_2$ or NR$^2$OR$^2$, wherein each R$^1$ is independently selected from the group consisting of alkyl, heteroalkyl, cycloalkyl, and cycloheteroalkyl, each of which is optionally substituted, or both R$^1$ are taken together with the attached nitrogen to form an optionally substituted heterocycle; wherein each R$^2$ is independently selected from the group consisting of a prodrug group, hydrogen, alkyl, alkyl heteroalkyl, cycloalkyl, and cycloheteroalkyl, each of which is optionally substituted.

2. The compound of claim 1 wherein R$^A$ represents benzo.

3. The compound of claim 1 wherein R is alkoxy.

4. The compound of claim 1 wherein R is methoxy.

5. The compound of claim 1 wherein X is alkyl substituted alkenylene.

6. The compound of claim 1 wherein X is CHCR$^X$, and R$^x$ is C1-C10 alkyl.

7. The compound of claim 1 wherein R$^x$ is C1-C9 alkyl.

8. The compound of claim 1 wherein R$^x$ is C1-C4 alkyl.

9. The compound of claim 1 wherein at least one R$^1$ is optionally substituted alkyl.

10. The compound of claim 1 wherein at least one R$^1$ is alkyl.

11. The compound of claim 1 wherein Y is NR$^2$OR$^2$, wherein each R$^2$ is independently selected from the group consisting of hydrogen, alkyl, alkyl heteroalkyl, cycloalkyl, and cycloheteroalkyl, each of which is optionally substituted, and a prodrug group, or both R$^2$ are taken together with the attached nitrogen and oxygen to form an optionally substituted heterocycle.

12. The compound of claim 11 wherein at least one R$^2$ is hydrogen.

13. The compound of claim 11 wherein at least one R$^2$ is optionally substituted alkyl.

14. The compound of claim 11 wherein at least one R$^2$ is alkyl.

15. The compound of claim 1 wherein R$^A$ is a benzo; R is a methoxy; X is an alkenylene which is optionally substituted; and Y is N(R$^1$)$_2$ wherein each R$^1$ is alkyl.

16. The compound of claim 1 being

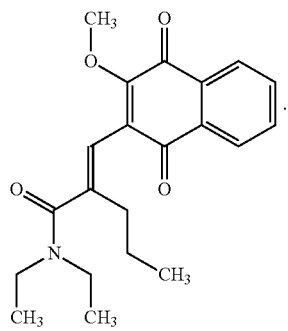 [SMILES: CCC/C(=C\C1=C(OC)C(=O)c2ccccc2C1=O)C(=O)N(CC)CC]

17. The compound of claim 1 wherein R$^A$ is a benzo; R is a methoxy; X is an alkenylene which is optionally substituted; and Y is NR$^2$OR$^2$ wherein R$^2$ is independently hydrogen and alkyl.

18. The compound of claim 1 being

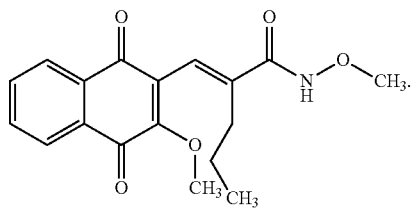 [SMILES: CCC/C(=C\C1=C(OC)C(=O)c2ccccc2C1=O)C(=O)NOC]

19. A compound for preventing or treating neuronal damage in a host animal, the compound having the formula

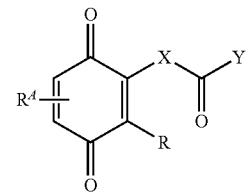

or a pharmaceutically acceptable salt thereof, wherein:
R$^A$ represents a fused aryl ring that is optionally substituted;
R is alkoxy, heteroalkoxy, cycloalkoxy, or cycloheteroalkoxy, each of which is optionally substituted;
X is a alkylene, alkenylene, or alkynylene, each of which is C$_3$-C$_9$ alkyl substituted; and
Y is a carboxylic acid or ester.

* * * * *